United States Patent
Shelton, IV

(10) Patent No.: US 9,326,768 B2
(45) Date of Patent: *May 3, 2016

(54) STAPLE CARTRIDGES FOR FORMING STAPLES HAVING DIFFERING FORMED STAPLE HEIGHTS

(71) Applicant: Ethicon Endo-Surgery, Inc., Cincinnati, OH (US)

(72) Inventor: Frederick E. Shelton, IV, Hillsboro, OH (US)

(73) Assignee: Ethicon Endo-Surgery, LLC, Los Frailes Industrial Park, Guaynabo, PR (US)

( * ) Notice: Subject to any disclaimer, the term of this patent is extended or adjusted under 35 U.S.C. 154(b) by 487 days.

This patent is subject to a terminal disclaimer.

(21) Appl. No.: 13/795,122

(22) Filed: Mar. 12, 2013

(65) Prior Publication Data

US 2013/0186936 A1     Jul. 25, 2013

Related U.S. Application Data

(63) Continuation of application No. 12/695,359, filed on Jan. 28, 2010, now Pat. No. 8,464,923, which is a continuation of application No. 11/216,562, filed on Aug. 31, 2005, now Pat. No. 7,669,746.

(51) Int. Cl.

| | |
|---|---|
| *A61B 17/068* | (2006.01) |
| *A61B 17/072* | (2006.01) |
| *B25C 5/02* | (2006.01) |

(52) U.S. Cl.
CPC .......... *A61B 17/0682* (2013.01); *A61B 17/072* (2013.01); *A61B 17/07207* (2013.01);
(Continued)

(58) Field of Classification Search
CPC ... A61B 17/068; A61B 17/072; A61B 17/115

USPC ...................... 227/175.1, 176.1, 178.1, 181.1
See application file for complete search history.

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2008207624 A1 | 3/2009 |
|---|---|---|
| AU | 2010214687 A1 | 9/2010 |

(Continued)

OTHER PUBLICATIONS

Petition for Inter Partes Review of U.S. Pat. No. 8,317,070, filed Mar. 25, 2013; IPR 2013-00209.

(Continued)

*Primary Examiner* — Nathaniel Chukwurah

(57) ABSTRACT

A staple cartridge for use with a stapling device that has an actuator that is selectively actuatable in an axial direction and an anvil portion that is selectively movable between open and closed positions is disclosed. Various embodiments of the present invention include a cartridge body that movably supports first and second staple drivers. The staple drivers each support a staple thereon and serve to drive the staples into forming contact with the anvil upon actuation by the actuator. The various embodiments of the present invention enable the final formed heights of the staples to be varied without the need to use different sizes of staples.

21 Claims, 27 Drawing Sheets

(52) U.S. Cl.
CPC ..... *B25C5/0292* (2013.01); *A61B 2017/07242* (2013.01); *A61B 2017/07264* (2013.01); *A61B 2017/07278* (2013.01)

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Siegel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |

(56) References Cited

U.S. PATENT DOCUMENTS

| | | | |
|---|---|---|---|
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A * | 7/1990 | Pruitt | A61B 17/072 227/175.1 |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |

(56) References Cited

U.S. PATENT DOCUMENTS

| | | |
|---|---|---|
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |

(56) References Cited

U.S. PATENT DOCUMENTS

| | | |
|---|---|---|
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |

(56) References Cited

U.S. PATENT DOCUMENTS

| | | |
|---|---|---|
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,694,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |

(56) References Cited

U.S. PATENT DOCUMENTS

| | | |
|---|---|---|
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |

(56) References Cited

U.S. PATENT DOCUMENTS

| | | |
|---|---|---|
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |

(56) References Cited

U.S. PATENT DOCUMENTS

| | | |
|---|---|---|
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |

(56) References Cited

U.S. PATENT DOCUMENTS

| | | |
|---|---|---|
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |

(56) References Cited

U.S. PATENT DOCUMENTS

| | | |
|---|---|---|
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,287,682 B1 | 10/2007 | Ezzat et al. |
| 7,293,685 B2 | 11/2007 | Ehrenfels et al. |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |

(56) References Cited

U.S. PATENT DOCUMENTS

| | | |
|---|---|---|
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 * | 3/2010 | Shelton, IV ...... A61B 17/07207 227/175.1 |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |

(56) References Cited

U.S. PATENT DOCUMENTS

| | | |
|---|---|---|
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |

(56) References Cited

U.S. PATENT DOCUMENTS

| | | |
|---|---|---|
| 7,954,687 B2 | 6/2011 | Zemlok et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |

(56) References Cited

U.S. PATENT DOCUMENTS

| | | | |
|---|---|---|---|
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,881 B2 | 9/2013 | Cabiri et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |

(56) References Cited

U.S. PATENT DOCUMENTS

| | | |
|---|---|---|
| 8,540,131 B2 | 9/2013 | Swayze |
| 8,540,133 B2 | 9/2013 | Bedi et al. |
| 8,540,733 B2 | 9/2013 | Whitman et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,736 B2 | 1/2014 | Yates et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,213 B2 | 4/2014 | Shelton, IV et al. |
| 8,720,766 B2 | 5/2014 | Hess et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,808,294 B2 | 8/2014 | Fox et al. |
| 8,808,311 B2 | 8/2014 | Heinrich et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,911,426 B2 | 12/2014 | Coppeta et al. |
| 8,911,471 B2 | 12/2014 | Spivey et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,996,165 B2 | 3/2015 | Wang et al. |
| 8,998,058 B2 | 4/2015 | Moore et al. |

(56) References Cited

U.S. PATENT DOCUMENTS

| | | |
|---|---|---|
| 9,005,230 B2 | 4/2015 | Yates et al. |
| 9,016,542 B2 | 4/2015 | Shelton, IV et al. |
| 9,023,014 B2 | 5/2015 | Chowaniec et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Glieman |
| 9,089,330 B2 | 7/2015 | Widenhouse et al. |
| 9,095,339 B2 | 8/2015 | Moore et al. |
| 9,096,033 B2 | 8/2015 | Holop et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,883 B2 | 8/2015 | Aronhalt et al. |
| 9,113,884 B2 | 8/2015 | Shelton, IV et al. |
| 9,119,957 B2 | 9/2015 | Shelton, IV et al. |
| 9,125,654 B2 | 9/2015 | Aronhalt et al. |
| 9,125,662 B2 | 9/2015 | Shelton, IV |
| 9,138,225 B2 | 9/2015 | Huang et al. |
| 9,149,274 B2 | 10/2015 | Spivey et al. |
| 2001/0025183 A1 | 9/2001 | Shahidi |
| 2001/0044637 A1 | 11/2001 | Jacobs et al. |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0165541 A1 | 11/2002 | Whitman |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232199 A1* | 11/2004 | Shelton, IV ...... A61B 17/07207 227/175.2 |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |

(56) References Cited

U.S. PATENT DOCUMENTS

| | | |
|---|---|---|
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1* | 8/2005 | Whitman ............ A61B 17/115 606/219 |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0221700 A1 | 9/2007 | Ortiz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |

(56) References Cited

U.S. PATENT DOCUMENTS

| | | |
|---|---|---|
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0242610 A1 | 10/2009 | Shelton, IV et al. |
| 2009/0247901 A1 | 10/2009 | Zimmer |
| 2009/0248038 A1 | 10/2009 | Blumenkranz et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0270895 A1 | 10/2009 | Churchill et al. |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0186219 A1 | 7/2010 | Smith |
| 2010/0193566 A1 | 8/2010 | Schieb et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |

(56) References Cited

U.S. PATENT DOCUMENTS

| | | |
|---|---|---|
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0017801 A1 | 1/2011 | Zemlok et al. |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0147434 A1* | 6/2011 | Hueil ............. A61B 17/072 227/178.1 |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0288573 A1 | 11/2011 | Yates et al. |
| 2011/0290851 A1 | 12/2011 | Shelton, IV |
| 2011/0290856 A1 | 12/2011 | Shelton, IV et al. |
| 2011/0293690 A1 | 12/2011 | Griffin et al. |
| 2011/0295269 A1 | 12/2011 | Swensgard et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0080336 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080488 A1 | 4/2012 | Shelton, IV et al. |
| 2012/0080498 A1 | 4/2012 | Shelton, IV et al. |
| 2012/0083835 A1 | 4/2012 | Shelton, IV et al. |
| 2012/0089131 A1 | 4/2012 | Zemlok et al. |
| 2012/0110810 A1 | 5/2012 | Houser et al. |
| 2012/0116395 A1 | 5/2012 | Madan et al. |
| 2012/0125792 A1 | 5/2012 | Cassivi |
| 2012/0138658 A1 | 6/2012 | Ullrich et al. |
| 2012/0150192 A1 | 6/2012 | Dachs, II et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0209289 A1 | 8/2012 | Duque et al. |
| 2012/0223123 A1 | 9/2012 | Baxter, III et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0238823 A1 | 9/2012 | Hagerty et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0075449 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126582 A1 | 5/2013 | Shelton, IV et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |

(56) References Cited

U.S. PATENT DOCUMENTS

| | | |
|---|---|---|
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005702 A1 | 1/2014 | Timm et al. |
| 2014/0005703 A1 | 1/2014 | Stulen et al. |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0061280 A1 | 3/2014 | Ingmanson et al. |
| 2014/0097227 A1 | 4/2014 | Aronhalt et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0151431 A1 | 6/2014 | Hodgkinson et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |

(56) References Cited

U.S. PATENT DOCUMENTS

| | | |
|---|---|---|
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305993 A1 | 10/2014 | Timm et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0090765 A1 | 4/2015 | Hess et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0144678 A1 | 5/2015 | Hall et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |

(56) References Cited

U.S. PATENT DOCUMENTS

| | | | |
|---|---|---|---|
| 2015/0297231 | A1 | 10/2015 | Huitema et al. |
| 2015/0297232 | A1 | 10/2015 | Huitema et al. |
| 2015/0297233 | A1 | 10/2015 | Huitema et al. |
| 2015/0297234 | A1 | 10/2015 | Schellin et al. |
| 2015/0297235 | A1 | 10/2015 | Harris et al. |
| 2015/0297236 | A1 | 10/2015 | Harris et al. |

FOREIGN PATENT DOCUMENTS

| | | | |
|---|---|---|---|
| AU | 2012200178 | B2 | 7/2013 |
| CA | 2458946 | A1 | 3/2003 |
| CA | 2477181 | A1 | 4/2004 |
| CA | 2512960 | A1 | 1/2006 |
| CA | 2514274 | A1 | 1/2006 |
| CA | 2639177 | A1 | 2/2009 |
| CN | 1163558 | A | 10/1997 |
| CN | 2488482 | Y | 5/2002 |
| CN | 1523725 | A | 8/2004 |
| CN | 1545154 | A | 11/2004 |
| CN | 1634601 | A | 7/2005 |
| CN | 2716900 | Y | 8/2005 |
| CN | 2738962 | Y | 11/2005 |
| CN | 1726874 | A | 2/2006 |
| CN | 1868411 | A | 11/2006 |
| CN | 1915180 | A | 2/2007 |
| CN | 2868212 | Y | 2/2007 |
| CN | 1960679 | A | 5/2007 |
| CN | 101011286 | A | 8/2007 |
| CN | 101095621 | A | 1/2008 |
| CN | 101541251 | A | 9/2009 |
| CN | 101675898 | A | 3/2010 |
| CN | 101683280 | A | 3/2010 |
| CN | 102188270 | A | 9/2011 |
| CN | 101534723 | B | 1/2012 |
| CN | 101507633 | B | 2/2013 |
| CN | 101023879 | B | 3/2013 |
| CN | 101401736 | B | 6/2013 |
| DE | 273689 | C | 5/1914 |
| DE | 1775926 | A | 1/1972 |
| DE | 3036217 | A1 | 4/1982 |
| DE | 3212828 | A1 | 11/1982 |
| DE | 3210466 | A1 | 9/1983 |
| DE | 3709067 | A1 | 9/1988 |
| DE | 9412228 | U | 9/1994 |
| DE | 19509116 | A1 | 9/1996 |
| DE | 19851291 | A1 | 1/2000 |
| DE | 19924311 | A1 | 11/2000 |
| DE | 69328576 | T2 | 1/2001 |
| DE | 20016423 | U1 | 2/2001 |
| DE | 10052679 | A1 | 5/2001 |
| DE | 20112837 | U1 | 10/2001 |
| DE | 20121753 | U1 | 4/2003 |
| DE | 10314072 | A1 | 10/2004 |
| DE | 202007003114 | U1 | 6/2007 |
| EP | 0000756 | A1 | 2/1979 |
| EP | 0122046 | A1 | 10/1984 |
| EP | 0070230 | B1 | 10/1985 |
| EP | 0156774 | A2 | 10/1985 |
| EP | 0033548 | B1 | 5/1986 |
| EP | 0077262 | B1 | 8/1986 |
| EP | 0129442 | B1 | 11/1987 |
| EP | 0276104 | A2 | 7/1988 |
| EP | 0379721 | B1 | 8/1990 |
| EP | 0178940 | B1 | 1/1991 |
| EP | 0178941 | B1 | 1/1991 |
| EP | 0169044 | B1 | 6/1991 |
| EP | 0248844 | B1 | 1/1993 |
| EP | 0539762 | A1 | 5/1993 |
| EP | 0545029 | A1 | 6/1993 |
| EP | 0548998 | A1 | 6/1993 |
| EP | 0277959 | B1 | 10/1993 |
| EP | 0591946 | A1 | 10/1993 |
| EP | 0233940 | B1 | 11/1993 |
| EP | 0261230 | B1 | 11/1993 |
| EP | 0639349 | A2 | 2/1994 |
| EP | 0324636 | B1 | 3/1994 |
| EP | 0593920 | A1 | 4/1994 |
| EP | 0594148 | A1 | 4/1994 |
| EP | 0427949 | B1 | 6/1994 |
| EP | 0523174 | B1 | 6/1994 |
| EP | 0600182 | A2 | 6/1994 |
| EP | 0310431 | B1 | 11/1994 |
| EP | 0375302 | B1 | 11/1994 |
| EP | 0376562 | B1 | 11/1994 |
| EP | 0630612 | A1 | 12/1994 |
| EP | 0634144 | A1 | 1/1995 |
| EP | 0646356 | A2 | 4/1995 |
| EP | 0646357 | A1 | 4/1995 |
| EP | 0505036 | B1 | 5/1995 |
| EP | 0653189 | A2 | 5/1995 |
| EP | 0669104 | A1 | 8/1995 |
| EP | 0387980 | B1 | 10/1995 |
| EP | 0511470 | B1 | 10/1995 |
| EP | 0674876 | A2 | 10/1995 |
| EP | 0679367 | A2 | 11/1995 |
| EP | 0392547 | B1 | 12/1995 |
| EP | 0685204 | A1 | 12/1995 |
| EP | 0364216 | B1 | 1/1996 |
| EP | 0699418 | A1 | 3/1996 |
| EP | 0702937 | A1 | 3/1996 |
| EP | 0488768 | B1 | 4/1996 |
| EP | 0705571 | A1 | 4/1996 |
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0737446 | A1 | 10/1996 |
| EP | 0748614 | A1 | 12/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0621009 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0869104 | A1 | 10/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0640317 | A1 | 9/1999 |
| EP | 0843906 | B1 | 3/2000 |
| EP | 0552050 | B1 | 5/2000 |
| EP | 0833592 | B1 | 5/2000 |
| EP | 0832605 | B1 | 6/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1058177 | A1 | 12/2000 |
| EP | 1080694 | A1 | 3/2001 |

(56) References Cited

FOREIGN PATENT DOCUMENTS

| | | |
|---|---|---|
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1769756 A1 | 4/2007 |
| EP | 1769758 A1 | 4/2007 |
| EP | 1581128 A1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |

(56) References Cited

FOREIGN PATENT DOCUMENTS

| | | | |
|---|---|---|---|
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 1935351 B1 | 9/2012 |
| EP | 2497431 A1 | 9/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 93100110 A | 11/1993 |
| JP | 50-33988 U | 4/1975 |

(56) References Cited

FOREIGN PATENT DOCUMENTS

| | | |
|---|---|---|
| JP | S 58500053 A | 1/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-334412 A | 12/2006 |
| JP | 2006-334417 A | 12/2006 |
| JP | 2006-346445 A | 12/2006 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |

(56) References Cited

FOREIGN PATENT DOCUMENTS

| | | |
|---|---|---|
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2010-504808 A | 2/2010 |
| JP | 2010-504809 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |

(56) References Cited

FOREIGN PATENT DOCUMENTS

| | | |
|---|---|---|
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A2 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |

(56) References Cited

FOREIGN PATENT DOCUMENTS

| WO | WO 2008/101228 A2 | 8/2008 |
|---|---|---|
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/143913 A2 | 10/2012 |
| WO | WO 2012/148667 A2 | 11/2012 |
| WO | WO 2012/148703 A2 | 11/2012 |
| WO | WO 2013/043707 A2 | 3/2013 |
| WO | WO 2013/043717 A1 | 3/2013 |
| WO | WO 2013/043721 A2 | 3/2013 |
| WO | WO 2013/148762 A2 | 10/2013 |
| WO | WO 2013/167427 A1 | 11/2013 |

OTHER PUBLICATIONS

Declaration of Henry Bolanos, Covidien Exhibit 1010, filed Mar. 25, 2013; IPR 2013-00209.
Curriculum Vitae of Henry Bolanos, Covidien Exhibit 1011, filed Mar. 25, 2013; IPR 2013-00209.
Excerpts from The American Heritage® College Dictionary, Fourth Edition, Copyright 2002, Covidien Exhibit 1016, filed Mar. 25, 2013; IPR 2013-00209.
Excerpts from Webster's II New College Dictionary, Third Edition, Copyright 2005, Covidien Exhibit 1017, filed Mar. 25, 2013; IPR 2013-00209.
Excerpts from Merriam-Webster's Collegiate® Dictionary, Eleventh Edition, Copyright 2005, Covidien Exhibit 1018, filed Mar. 25, 2013; IPR 2013-00209.
Ethicon Endo-Surgery, Inc.'s Mandatory Notices, filed Apr. 12, 2013; IPR 2013-00209.
Ethicon Endo-Surgery, Inc.'s Preliminary Response, filed Jun. 21, 2013; IPR 2013-00209.
Decision, Institution of Inter Partes Review 37 C.F.R. § 42.108, dated Aug. 26, 2013; IPR 2013-00209.
Petitioner's Request for Rehearing Under 37 C.F.R. § 42.71(d), filed Sep. 9, 2013; IPR 2013-00209.
Decision, Petitioner's Request for Rehearing 37 C.F.R. § 42.71, dated Sep. 20, 2013; IPR 2013-00209.
Ethicon Endo-Surgery, Inc.'s Patent Owner Response Pursuant to 37 C.F.R. § 42.120, filed Nov. 19, 2013; IPR 2013-00209.
Expert Declaration of Mark S. Ortiz, Ethicon Exhibit 2004, filed Nov. 19, 2013; IPR 2013-00209.
Resume of Mark S. Ortiz, Ethicon Exhibit 2005, filed Nov. 19, 2013; IPR 2013-00209.
Covidien's Nov. 24, 2008 510(k) Summary of Safety and Effectiveness, Ethicon Exhibit 2013, filed Nov. 19, 2013; IPR 2013-00209.
Covidien Technical Brochure: Endo GIA™ Reloads with Tri-Staple™ Technology, Ethicon Exhibit 2014, filed Nov. 19, 2013; IPR 2013-00209.
Claim Chart—U.S. Pat. No. 8,317,070, Exhibit 2015, filed Nov. 19, 2013; IPR 2013-00209.
Jan. 7, 2013 Covidien News Release "Covidien's Tri-Staple™ Technology Platform Reaches $1 Billion Sales Milestone", Ethicon Exhibit 2016, filed Nov. 19, 2013; IPR 2013-00209.
IMS Raw Data, Ethicon Exhibit 2017, filed Nov. 19, 2013; IPR 2013-00209.
Covidien Tri-Staple™ Brochure, Ethicon Exhibit 2018, filed Nov. 19, 2013; IPR 2013-00209.
2012 Covidien Annual Report, Ethicon Exhibit 2019, filed Nov. 19, 2013; IPR 2013-00209.
IMS Pricing, Ethicon Exhibit 2021, filed Nov. 19, 2013; IPR 2013-00209.
IMS Unit Data, Ethicon Exhibit 2022, filed Nov. 19, 2013; IPR 2013-00209.
Covidien Website—Endo GIA™ Ultra Universal Staplers and Reloads, Ethicon Exhibit 2023, filed Nov. 19, 2013; IPR 2013-00209.
Covidien Technical Brochure: Endo GIA™ Reloads with Tri-Staple™ Technology and Endo GIA™ Ultra Universal Staplers, Ethicon Exhibit 2024, filed Nov. 19, 2013; IPR 2013-00209.
Ethicon Endo-Surgery, Inc.'s Updated Mandatory Notices, filed Dec. 9, 2013; IPR 2013-00209.
Petitioner's Reply Under 37 C.F.R. § 42.23 to Patent Owner Response, filed Feb. 5, 2014; IPR 2013-00209.
Petitioner's Current List of Exhibits, filed Feb. 5, 2014; IPR 2013-00209.
Transcript from Deposition of Henry Bolanos taken Nov. 7, 2013, Covidien Exhibit 1019, filed Feb. 5, 2014; IPR 2013-00209.
Transcript from Deposition of Mark S. Ortiz taken Jan. 15, 2014, Covidien Exhibit 1023, filed Feb. 5, 2014; IPR 2013-00209.
Patent Owner's Response filed Jun. 2, 2008, in European Patent Application No. 06254511.6, Covidien Exhibit 1024, filed Feb. 5, 2014; IPR 2013-00209.
Communication from the European Patent Office dated Jan. 24, 2007, in European Patent Application No. 06254511.6, Covidien Exhibit 1025, filed Feb. 5, 2014; IPR 2013-00209.
Communication from the European Patent Office dated Feb. 13, 2008, in European Patent Application No. 06254511.6, Covidien Exhibit 1026, filed Feb. 5, 2014; IPR 2013-00209.
Patent Owner Response filed Jun. 29, 2011, in European Patent Application No. 10178489.0, Covidien Exhibit 1027, filed Feb. 5, 2014; IPR 2013-00209.
Communication from the European Patent Office dated Nov. 29, 2010, in European Patent Application No. 10178489.0, Covidien Exhibit 1028, filed Feb. 5, 2014; IPR 2013-00209.
Patent Owner's Response filed Jul. 26, 2011, in European Patent Application No. 10179946.8, Covidien Exhibit 1029, filed Feb. 5, 2014; IPR 2013-00209.
Communication from the European Patent Office dated Dec. 2, 2010, in European Patent Application No. 10179946.8, Covidien Exhibit 1030, filed Feb. 5, 2014; IPR 2013-00209.
Rebuttal Declaration of Henry Bolanos, Covidien Exhibit 1031, filed Feb. 5, 2014; IPR 2013-00209.
Patent Owner's Submission dated Mar. 1, 2010 from a suit in Germany relating to European Patent No. EP 0 337 612 (German Patent No. DE 689 07 255)(including English-language translation and Certificate of Translation), Covidien Exhibit 1032, filed Feb. 5, 2014; IPR 2013-00209.
Expert Report of William David Kelly dated Feb. 8, 2006 from a suit in Germany relating to European Patent No. EP 0 337 612 (German Patent No. DE 689 07 255), Covidien Exhibit 1033, filed Feb. 5, 2014; IPR 2013-00209.

(56) References Cited

OTHER PUBLICATIONS

Petitioner's Demonstrative Exhibits, filed Apr. 7, 2014; IPR 2013-00209.
Patent Owner's Demonstrative Exhibits, filed Apr. 7, 2014; IPR 2013-00209.
Oral Hearing Transcript, held Apr. 10, 2014, entered May 9, 2014; IPR 2013-00209.
Final Written Decision 35 U.S.C. § 318(a) and 37 C.F.R. § 42.73, entered Jun. 9, 2014; IPR 2013-00209.
Ethicon Endo-Surgery, Inc.'s Notice of Appeal, filed Aug. 5, 2014; IPR 2013-00209.
European Examination Report, Application No. 08250671.8, dated Mar. 24, 2009 (6 pages).
European Examination Report, Application No. 08250668.4, dated Mar. 19, 2015 (5 pages).
European Examination Report, Application No. 06254511.6, dated Feb. 13, 2008 (5 pages).
European Examination Report, Application No. 06254511.6, dated Feb. 9, 2015 (5 pages).
European Examination Report, Application No. 08250661.9, dated Feb. 24, 2010 (6 pages).
European Examination Report, Application 08250664.3, dated Feb. 24, 2010 (6 pages).
European Examination Report, Application 08250668.4, dated Dec. 10, 2009 (5 pages).
European Examination Report for 08250671.8, dated Nov. 21, 2012 (5 pages).
Observations by a Third Party, European Application No. 06254511.6, dated Feb. 7, 2008 (4 pages).
International Search Report and Written Opinion for PCT/US2012/039134, Aug. 31, 2012 (11 pages).
European Search Report, Application No. 08250668.4, dated May 4, 2009 (7 pages).
Partial European Search Report, Application No. 08250661.9, dated May 7, 2009 (6 pages).
European Search Report, Application No. 08250667.6, dated May 14, 2009 (6 pages).
Partial European Search Report, Application No. 08250664.3, dated May 7, 2009 (6 pages).
European Search Report, Application No. 10178489.0, dated Nov. 29, 2010 (7 pages).
European Search Report, Application No. 10179946.8, dated Dec. 2, 2010 (7 pages).
European Search Report, Application 08250671.8, dated May 19, 2008 (9 pages).
European Search Report, Application 06254511.6, dated Jan. 24, 2007 (8 pages).
European Search Report, Application No. 08250661.9, dated Jul. 28, 2009 (12 pages).
European Search Report, Application No. 11161037.4, dated Sep. 6, 2011 (9 pages).
European Search Report, Application No. 08250664.3, dated Jul. 28, 2009 (11 pages).
European Search Report, Application No. 11190802.6, dated Aug. 13, 2012 (8 pages).
International Preliminary Report on Patentability for PCT/US2012/039134, Dec. 2, 2013 (7 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.

(56) References Cited

OTHER PUBLICATIONS

Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
U.S. Appl. No. 12/031,573, filed Feb. 14, 2008.
U.S. Appl. No. 14/498,070, filed Sep. 26, 2014.
U.S. Appl. No. 14/498,087, filed Sep. 26, 2014.
U.S. Appl. No. 14/498,105, filed Sep. 26, 2014.
U.S. Appl. No. 14/498,107, filed Sep. 26, 2014.
U.S. Appl. No. 14/498,121, filed Sep. 26, 2014.
U.S. Appl. No. 14/498,145, filed Sep. 26, 2014.
U.S. Appl. No. 14/755,151, filed Jun. 30, 2015.
U.S. Appl. No. 14/847,804, filed Sep. 8, 2015.
U.S. Appl. No. 14/848,591, filed Sep. 9, 2015.
U.S. Appl. No. 14/850,570, filed Sep. 10, 2015.

\* cited by examiner

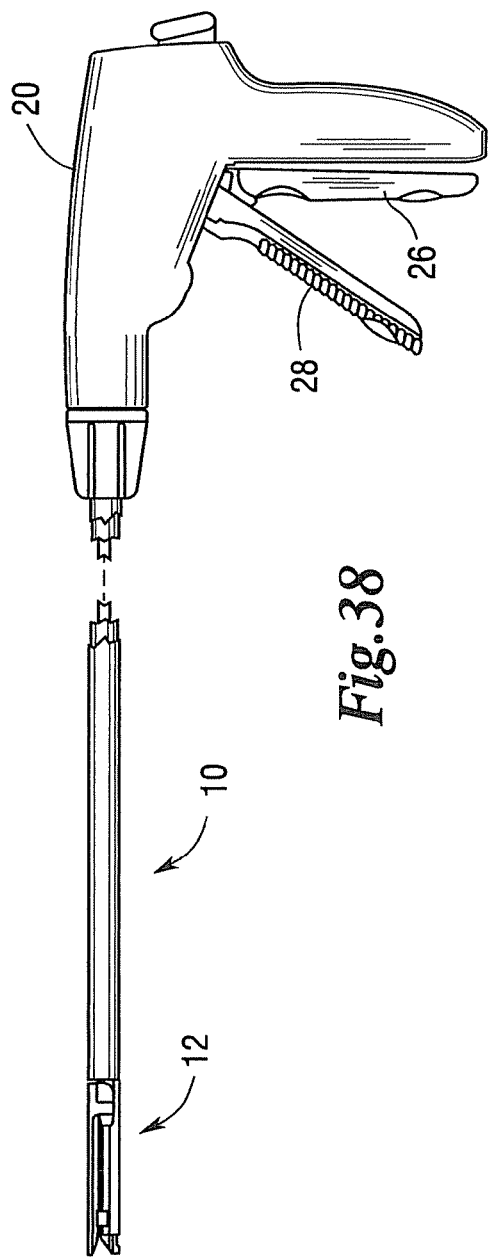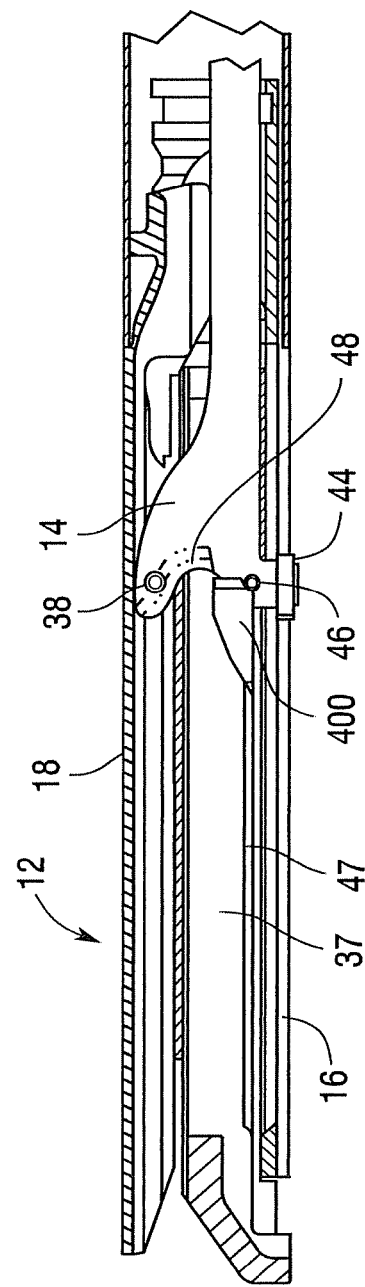
Fig.38
Fig.39

STAPLE CARTRIDGES FOR FORMING STAPLES HAVING DIFFERING FORMED STAPLE HEIGHTS

CROSS-REFERENCE TO RELATED APPLICATIONS

This application is a continuation application claiming priority under 35 U.S.C. §120 to U.S. patent application Ser. No. 12/695,359, entitled SURGICAL STAPLING DEVICES FOR FORMING STAPLES WITH DIFFERENT FORMED HEIGHTS, filed on Jan. 28, 2010, now U.S. Pat. No. 8,464,923, the entire disclosure of which is hereby incorporated by reference herein, which is a continuation under 35 U.S.C. §120 of U.S. patent application Ser. No. 11/216,562, entitled STAPLE CARTRIDGES FOR FORMING STAPLES HAVING DIFFERING FORMED STAPLE HEIGHTS, filed Aug. 31, 2005, now U.S. Pat. No. 7,669,746, the entire disclosure of which is hereby incorporated by reference herein.

FIELD OF THE INVENTION

The present invention relates in general to stapling instruments that are capable of applying lines of staples and, more particularly, to improvements relating to staple cartridges for use with surgical stapling instruments that are capable of applying lines of staples having differing formed staple heights to tissue while simultaneously cutting the tissue.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil.

An example of a surgical stapler suitable for endoscopic applications is described in U.S. Patent Application Publication No. 2004/0232196 A1, now U.S. Pat. No. 7,000,818, the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

Whenever a transection of tissue is across an area of varied tissue composition, it would be advantageous for the staples that are closest to the cut line to have one formed height that is less than the formed height of those staples that are farthest from the cut line. In practice, the rows of inside staples serve to provide a hemostatic barrier, while the outside rows of staples with larger formed heights provide a cinching effect where the tissue transitions from the tightly compressed hemostatic section to the non-compressed adjacent section. In other applications, it may be useful for the staples in a single line of staples to have differing formed heights.

U.S. Pat. Nos. 4,941,623 and 5,027,834 to Pruitt disclose surgical stapler and cartridge arrangements that employ staples that have different prong lengths to ultimately achieve lines of staples that have differing formed heights. Likewise, WO 2003/094747A1 discloses a surgical stapler and cartridge that has six rows of staples wherein the outer two rows of staples comprise staples that are larger than the staples employed in the inner two rows and middle rows of staples. Thus, all of these approaches require the use of different sizes of staples in the same cartridge.

Consequently, a significant need exists for an improved cartridge for a stapling instrument that can form lines of staples that have differing formed heights without the need to employ different sizes of staples in the same cartridge.

BRIEF SUMMARY OF THE INVENTION

In various embodiments, a surgical staple cartridge for use with a surgical stapling instrument that includes an anvil that includes at least one tissue stop portion thereon is provided. The surgical staple cartridge comprises a cartridge body configured to be operably seated in a cartridge supporting portion of the surgical stapling instrument to confront a staple forming surface on the anvil when the anvil is moved to a closed position, a plurality of first staple drivers movably supported within the cartridge body, each first staple driver defining a first staple support cradle for supporting a first surgical staple thereon to define a linear row of first surgical staples within the cartridge body, and a plurality of second staple drivers movably supported within the cartridge body, each second staple driver defining a second staple support cradle for supporting a second surgical staple thereon to define another linear row of second surgical staples within the cartridge body and wherein a proximal-most first driver and a proximal-most second driver are configured and positioned within the cartridge body such that at least a portion of one first surgical staple and at least a portion of one second surgical staple are located proximal to a distal end of at least one of the tissue stop portions on the anvil when the first and second surgical staples are driven into forming contact with the staple forming surface on the anvil and such that the first surgical staples have a formed staple height that differs from a formed height of the second surgical staples.

In various embodiments, a surgical staple cartridge for use with a surgical stapling instrument that includes an anvil that includes at least one tissue stop portion thereon is provided. The surgical staple cartridge comprises a cartridge body configured to be operably seated in a cartridge supporting portion of the surgical stapling instrument to confront a staple forming surface on the anvil when the anvil is moved to a closed position, the cartridge body including an elongate slot for receiving a cutting portion of the surgical stapling instrument, a plurality of first staple drivers operably supported in the cartridge body and configured to eject surgical staples into forming contact with the staple forming surface on the anvil in at least two linear rows located on at least one lateral side of the elongate slot such that at least a portion of a proximal-most surgical staple in each linear row is located proximal to a distal end of at least one of the tissue stop portions on the anvil when the surgical staples are ejected into forming contact with the staple forming surface on the anvil, and a plurality of second staple drivers movably supported in the cartridge body and configured to eject other surgical staples in another linear row located on the at least one lateral side of the elongate slot into forming contact with the staple forming surface on the anvil such that a proximal-most other surgical staple in the another linear row is distal to the distal end of the at least one tissue stop portion and wherein the other surgical staples ejected by the second staple drivers have a formed staple height that differs from a formed staple height of the surgical staples in at least one the linear row of surgical staples ejected by the first staple drivers.

In various embodiments, a surgical stapling device is provided. The surgical stapling device comprises a firing system for generating firing motions, a closure system for generating opening and closing motions, and an implement portion operably interfacing with the firing and closure systems. The implement portion comprises an elongate channel operably interfacing with the firing and closure systems and configured to support a staple cartridge therein, an anvil pivotally coupled to the elongate channel and being movable between open and closed positions relative to the elongate channel in response to closure and opening motions from the closure system, a firing device including a distally presented cutting edge longitudinally movable within the elongate channel in response to firing motions allied thereto by the firing system, and a staple cartridge. The staple cartridge comprises a cartridge body supportable within the elongate channel, the cartridge body having a non-planar deck surface configured to confront a staple forming portion of the anvil when the anvil is in a closed position, a plurality of first staple drivers movably supported within the cartridge body and being sequentially movable from an unactuated position to an actuated position upon sequential interaction with the firing device, each first staple driver defining a first staple support cradle therein for supporting a staple thereon, each first staple support cradle located a first staple forming distance from a corresponding portion of the staple forming portion of the closed anvil, and a plurality of second staple drivers movably supported within the cartridge body and being laterally spaced from the first staple drivers, each second staple driver being sequentially movable from another unactuated position to another actuated position upon sequential interaction with the firing device, each second staple driver defining a second staple support cradle therein for supporting another staple thereon, each second staple support cradle located a second staple forming distance from another corresponding portion of the staple forming portion of the closed anvil that corresponds to the second staple support cradle and wherein the second staple forming distance differs in magnitude from the first staple forming distance.

In various embodiments, a surgical stapling system is provided. The surgical stapling system comprises a firing system configured to generate a firing motion and an implement portion configurable in an open configuration and a clamped configuration. The implement portion comprises a distal end, an anvil comprising a staple forming portion, a firing member including a distally presented cutting edge movable toward the distal end in response to the firing motion generated by the firing system, and a staple cartridge. The staple cartridge comprises, one, a cartridge body comprising a non-planar deck surface configured to confront the staple forming portion of the anvil and, two, a plurality of staple drivers movably supported within the cartridge body, wherein the staple drivers are sequentially movable from an unactuated position to an actuated position by the firing member. The staple drivers comprise, one, a first longitudinal row of first staple support cradles, wherein each first staple support cradle is configured to support a first staple thereon, wherein the first staple support cradles are located a first staple forming distance from a first corresponding portion of the staple forming portion that corresponds to the first staple support cradles when the implement portion is in the clamped configuration and, two, a second longitudinal row of second staple support cradles, wherein each second staple support cradle is configured to support a second staple thereon, wherein the second staple support cradles are located a second staple forming distance from a second corresponding portion of the staple forming portion that corresponds to the second staple support cradles when the implement portion is in the clamped configuration, and wherein the second staple forming distance differs in magnitude from the first staple forming distance.

One feature of various embodiments of the present invention is to provide a staple cartridge for a stapling device that employs rows or other pluralities of identically sized staples while facilitating the ability of forming the staples with differing formed (final) heights. In some embodiments, the final heights may be varied across adjacent rows of staples. In other embodiments, the formed heights of the staples may be varied from staple to staple in a single row of staples. Accordingly, various embodiments of the invention provide solutions to the shortcomings of other staple cartridges and stapling devices that must employ different sizes of staples to achieve staples that have varying formed heights. Those of ordinary skill in the art will readily appreciate, however, that these and other details, features and advantages will become further apparent as the following detailed description proceeds.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 38 depicts a view in centerline section of the distal end of the surgical stapling and severing instrument of FIG. 1 in a partially fired position.

FIG. 39 depicts a partially cut away side elevation view of the surgical stapling and severing instrument of FIG. 1 in a partially fired position.

DETAILED DESCRIPTION OF THE INVENTION

Figure 1:
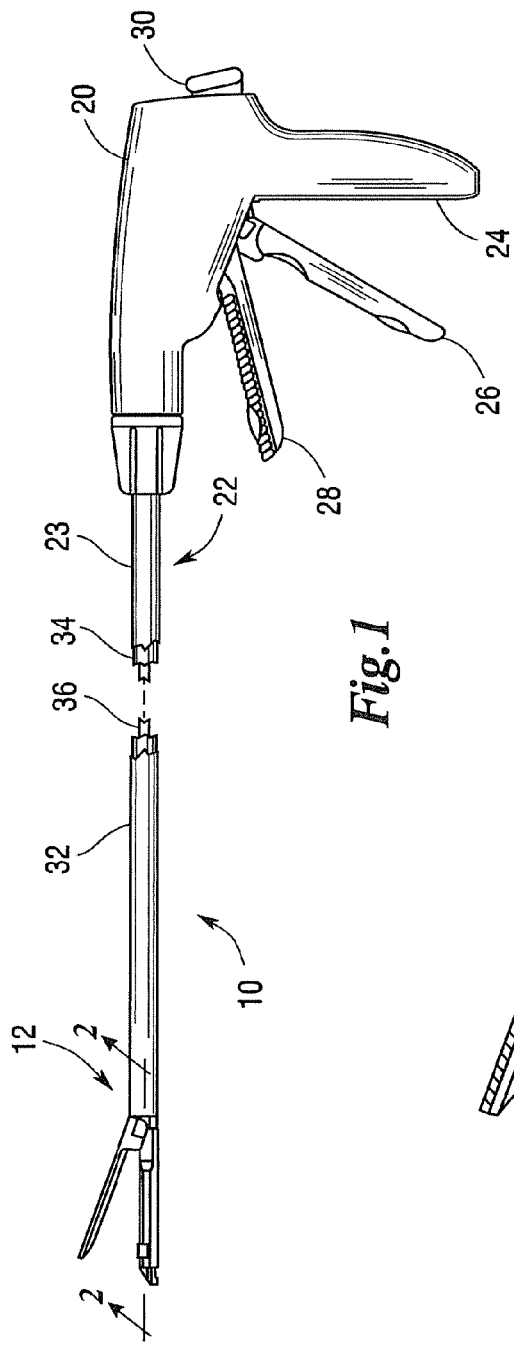
FIG. 1 depicts a partially cut away side elevation view of a surgical stapling and severing instrument in an open position.
Figure 2:
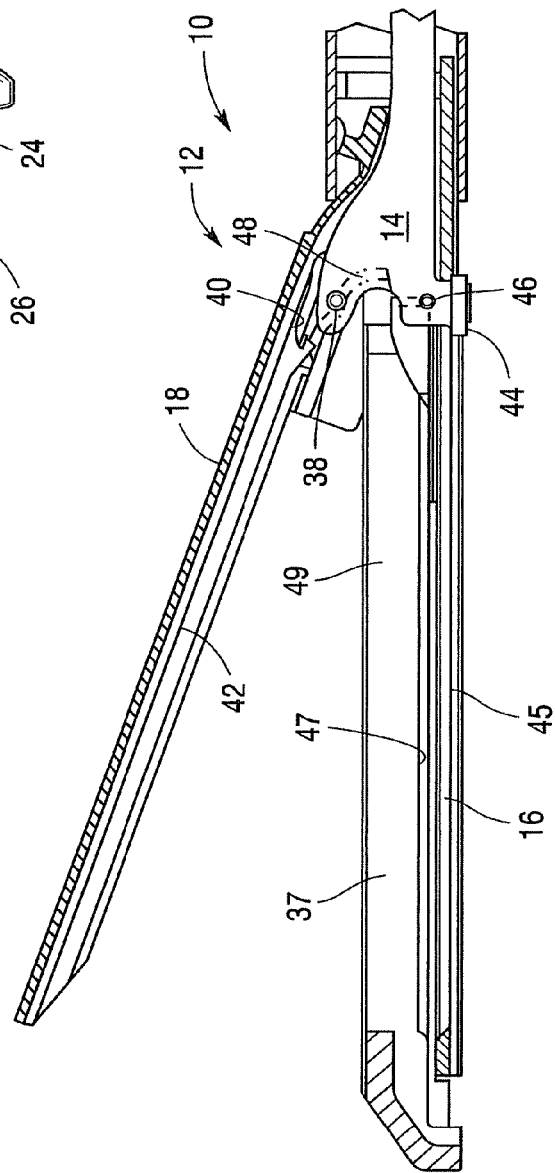
FIG. 2 depicts a cross-sectional side elevation detail view along the line 2-2 of FIG. 1 of an end effector of the surgical stapling and severing instrument.

Turning to the Drawings, wherein like numerals denote like components throughout the several views, FIGS. 1 and 2 depict one embodiment of a surgical stapling and severing instrument 10 that is capable of practicing the unique benefits of the present invention. As the present Detailed Description proceeds, the reader will appreciate, however, that the unique and novel aspects of the present invention may be advantageously employed in connection with a variety of other staplers and stapler instruments without departing from the spirit and scope of the present invention. Accordingly, the scope of protection afforded to the various embodiments of the present invention should not be limited to use only with the specific type of surgical stapling and severing instruments described herein.

As can be seen in FIGS. 1 and 2, the surgical stapling and severing instrument 10 incorporates an end effector 12 having an actuator or E-beam firing mechanism ("firing bar") 14 that advantageously controls the spacing of the end effector 12. In particular, an elongate channel 16 and a pivotally translatable anvil 18 are maintained at a spacing that assures effective stapling and severing. The problems are avoided associated with varying amounts of tissue being captured in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The surgical and stapling and severing instrument 10 includes a handle portion 20 that is connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

In practice, closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32. The elongate channel 16 receives a staple cartridge 37.

Figure 3:
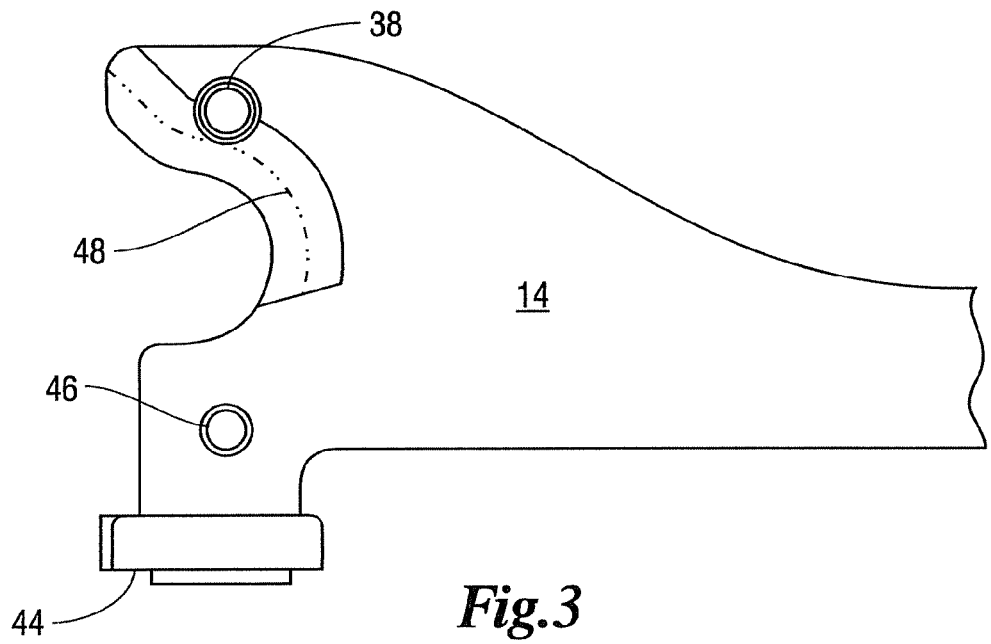
FIG. 3 depicts an enlarged side elevation view of the firing bar of the surgical stapling and severing instrument of FIG. 2.
Figure 4:
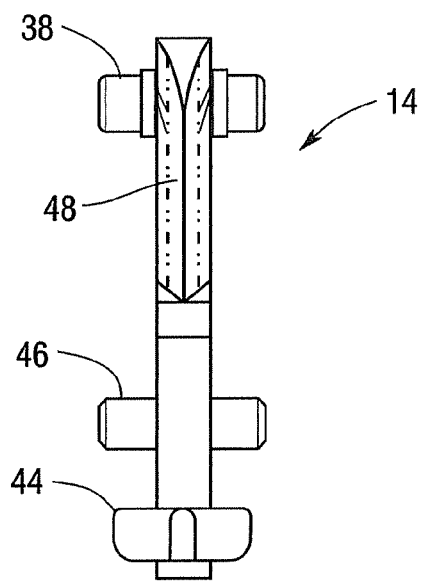
FIG. 4 depicts an enlarged front view of the firing bar of the surgical stapling and severing instrument of FIG. 2.

With particular reference to FIGS. 2-4, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38. Firing bar 14 also includes a lowermost pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween.

Figure 5:
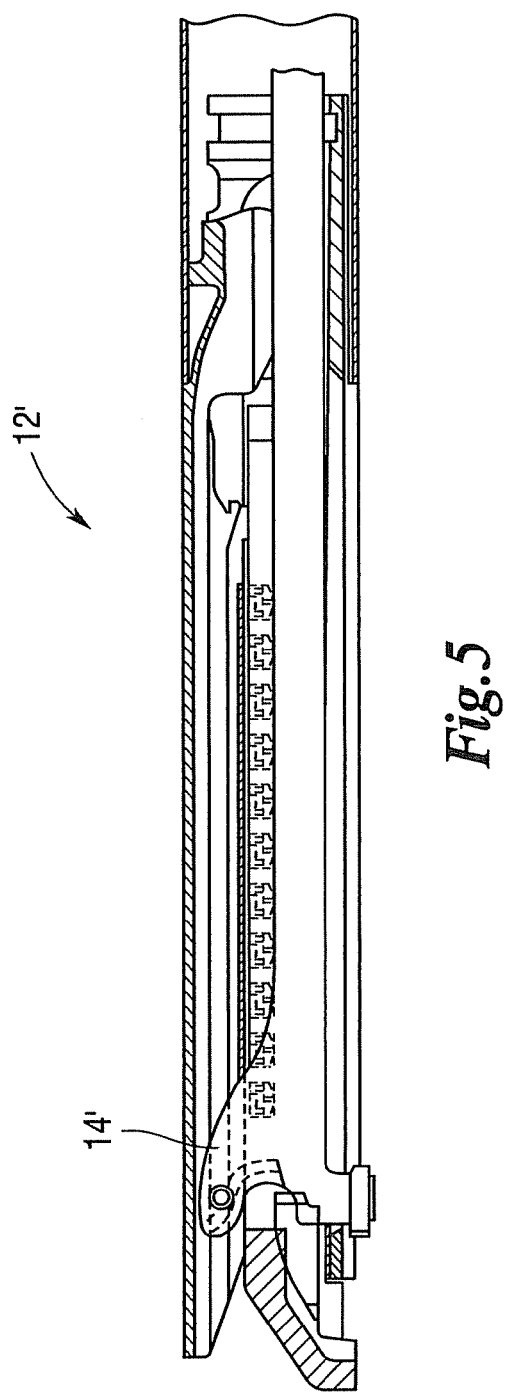
FIG. 5 depicts a cross-sectional side elevation detail view of an alternative end effector for the surgical stapling and severing instrument of FIG. 1, incorporating a firing bar that lacks a middle pin for preventing pinching of the end effector.

The firing bar 14 advantageously includes a middle pin 46 that passes through a firing drive slot 47 formed in a lower surface of the cartridge 300 and an upward surface of the elongate channel 16, thereby driving the staples therein as described below. The middle pin 46, by sliding against the elongate channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2-4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14 with regard to the elongate channel 16 and anvil 18 assure that an effective cut is performed.

The affirmative vertical spacing provided by the E-Beam firing bar 14 is suitable for the limited size available for endoscopic devices. Moreover, the E-Beam firing bar 14 enables fabrication of an anvil 15 with a camber imparting a vertical deflection at its distal end, similar to the position depicted in FIG. 5. This cambered anvil 15 advantageously assists in achieving the desired gap in the end effector 12 even with an anvil 15 having a reduced thickness, which may be more suited to the size limitations of an endoscopic device.

With reference to FIGS. 6-9, the handle portion 20 is comprised of first and second base sections 50 and 52, which are molded from a polymeric material such as a glass-filled polycarbonate. The first base section 50 is provided with a plurality of cylindrically-shaped pins 54. The second base section 52 includes a plurality of extending members 56, each having a hexagonal-shaped opening 58. The cylindrically-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6-9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72, extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32.

Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 100 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 8:
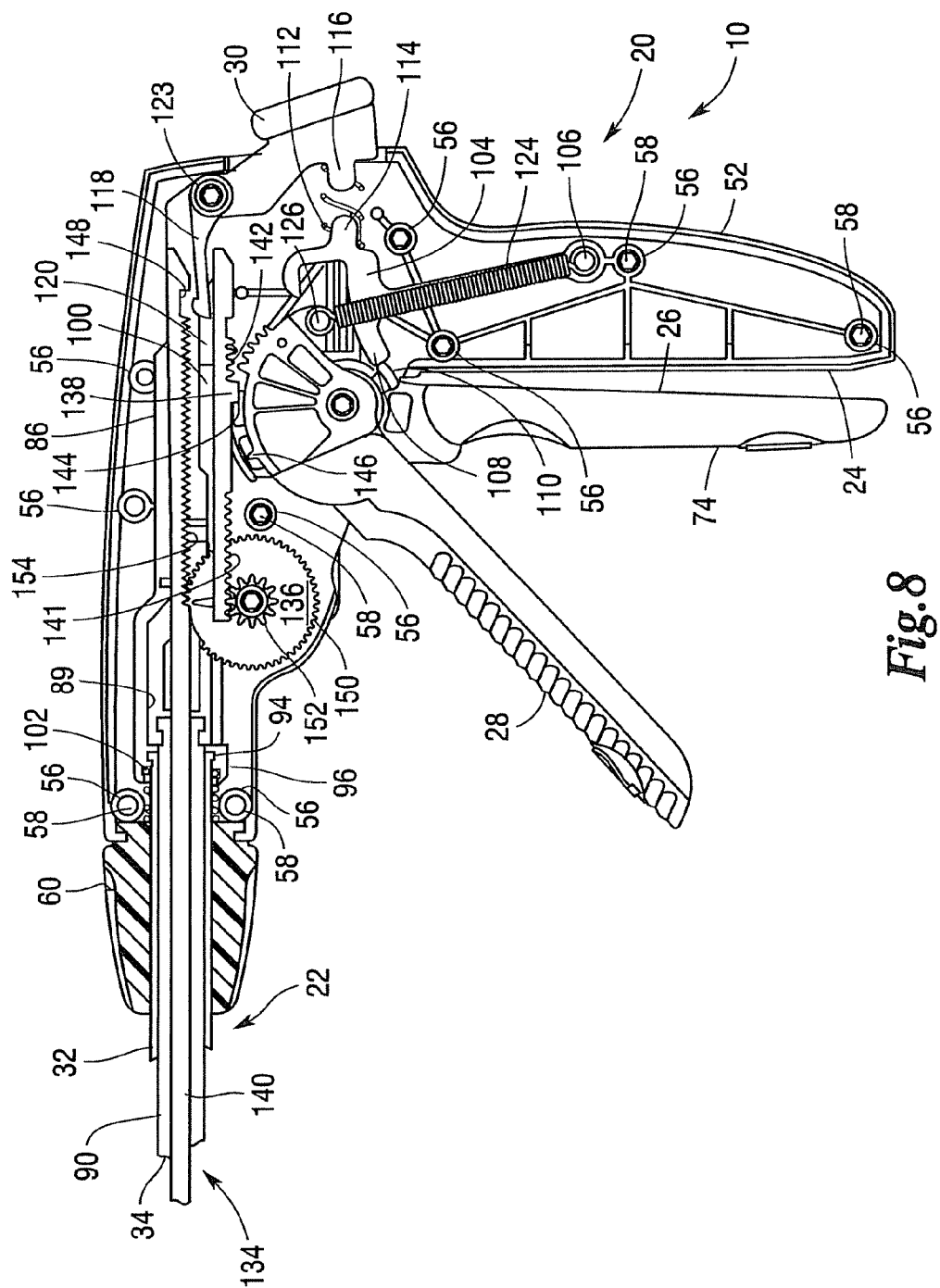
FIG. 8 depicts a side elevational view of the handle portion of the proximal end of the surgical stapling and severing instrument of FIG. 1 with the left side removed to expose interior parts in the closed ("clamped") position.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIGS. 6-9) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
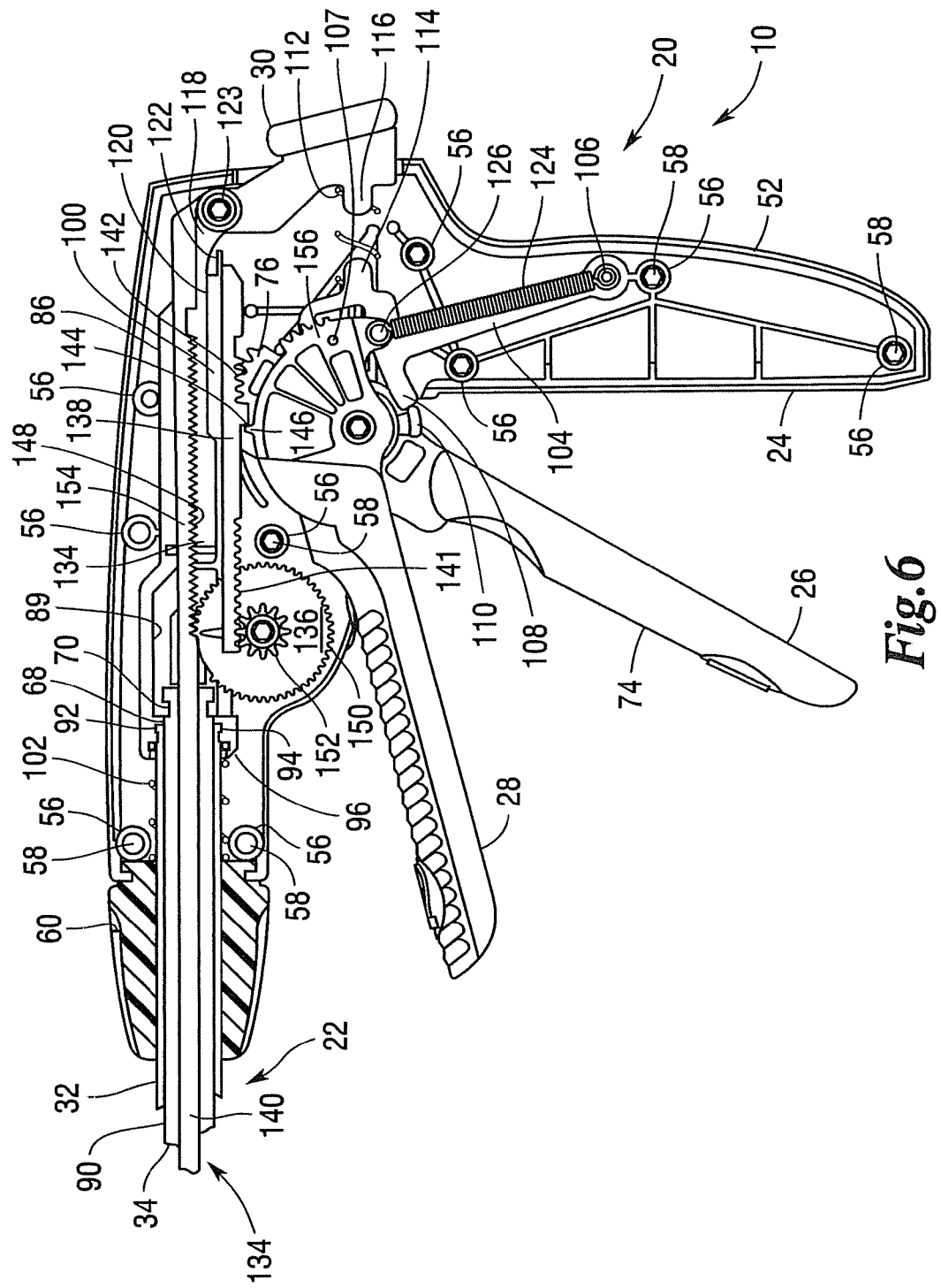
FIG. 6 depicts a side elevational view of a handle portion of a proximal end of the surgical stapling and severing instrument of FIG. 1 with a left side removed to expose interior parts in an unclamped, unfired ("start") position.
Figure 7:
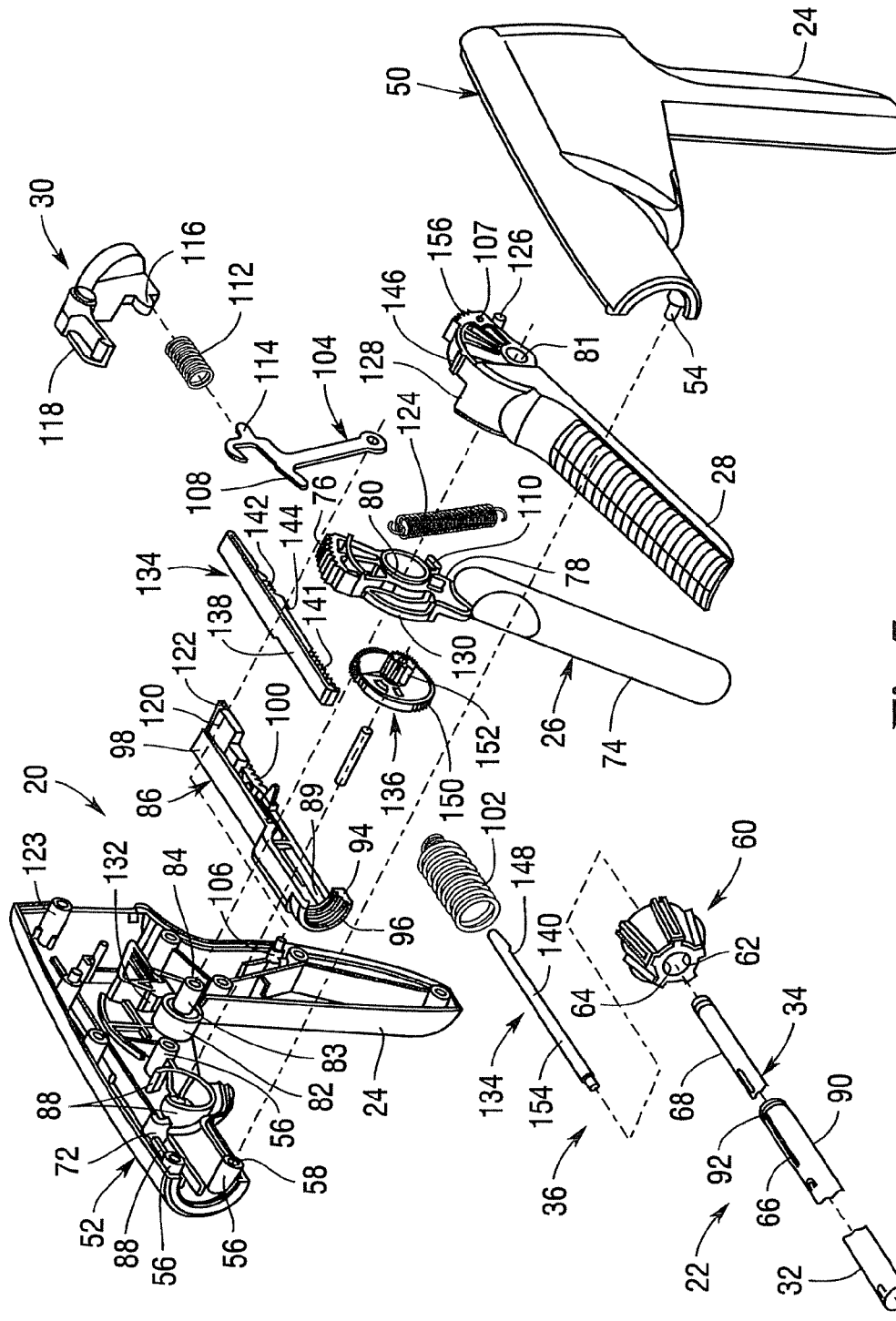
FIG. 7 depicts a perspective, exploded view of the handle portion of the proximal end of the surgical stapling and severing instrument of FIG. 1.
Figure 9:
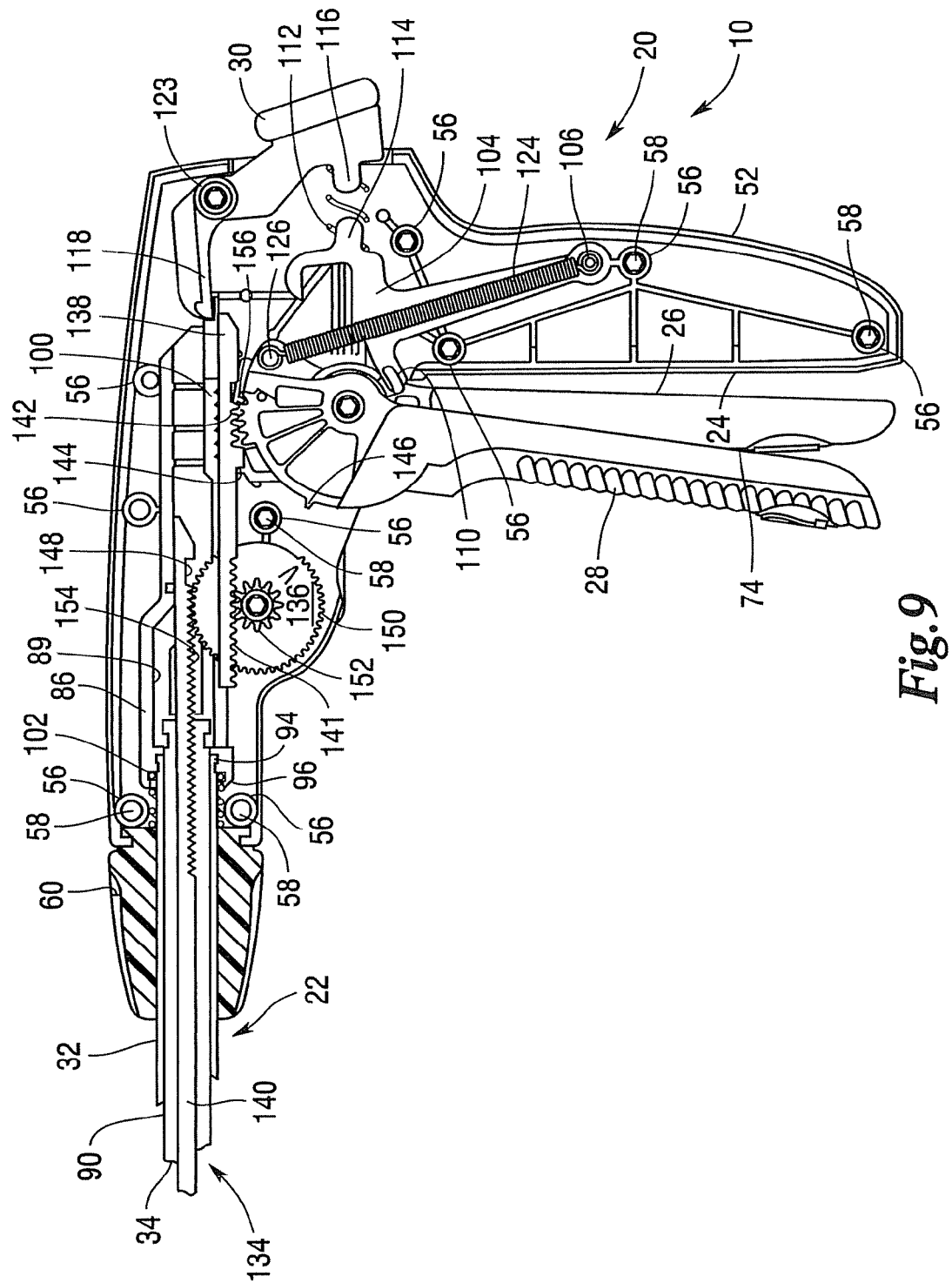
FIG. 9 depicts a side elevational view of the handle portion of proximal end of surgical stapling and severing instrument of FIG. 1 with the left side removed to expose interior parts in the stapled and severed ("fired") position.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 39 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied. It will be appreciated that the handle portion 20 is illustrative and that other actuation mechanisms may be employed. For instance, the closing and firing motions may be generated by automated means.

One embodiment of an end effector 12 of the surgical stapling and severing instrument 10 is depicted in further detail in FIGS. 18, 19, and 23-26. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
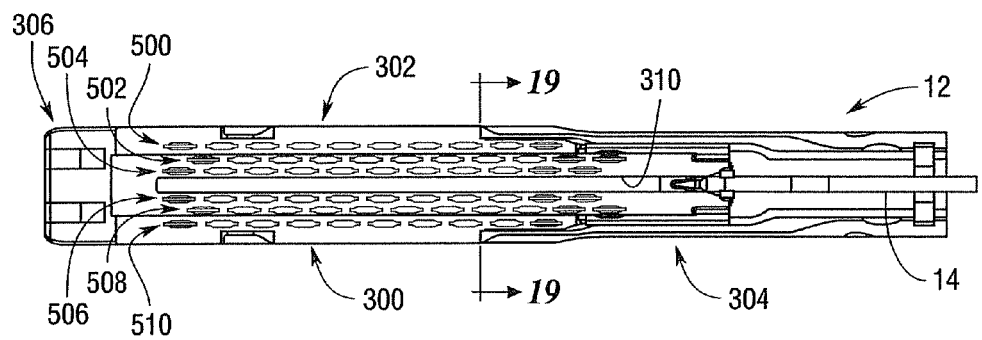
FIG. 10 depicts a plan view of a staple cartridge installed in an end effector of an embodiment of the present invention.

FIG. 10 depicts a staple cartridge embodiment 300 of the present invention installed in the end effector 12 with the firing bar 14 in its unfired, proximal position. The staple cartridge 300 has a cartridge body 302 that is divided by an elongated slot 310 that extends from a proximal end 304 of the cartridge 300 towards a tapered outer tip 306. A plurality of staple-receiving channels 320a-320f are formed within the staple cartridge body 302 and are arranged in six laterally spaced longitudinal rows 500, 502, 504, 506, 508, 510, with three rows on each side of the elongated slot 310. Positioned within the staple-receiving channels 320a-320f are the staples 222. See FIGS. 10 and 11.

Figure 11:
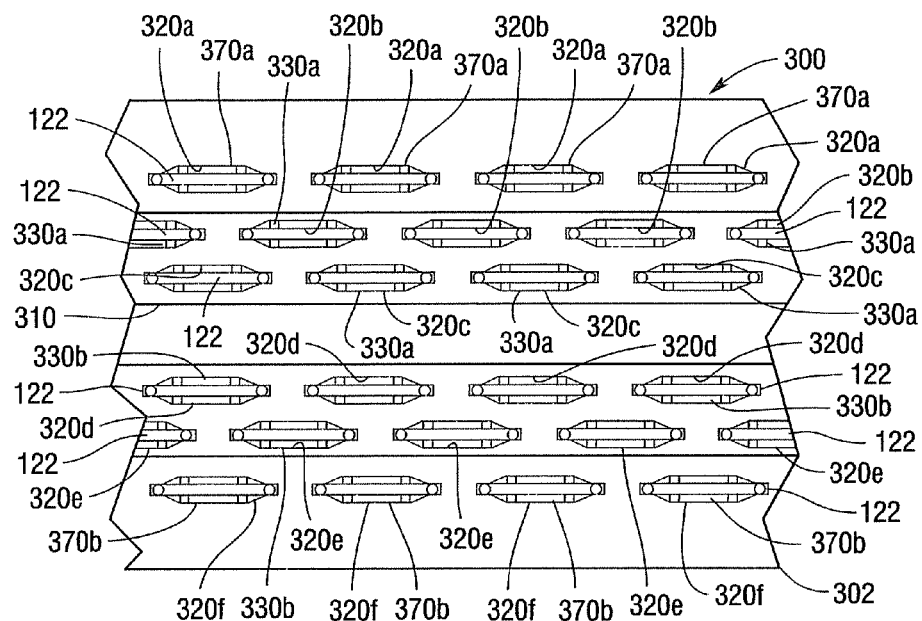
FIG. 11 is an enlarged plan view of a portion of a staple cartridge embodiment of the present invention.

The cartridge 300 further includes four laterally spaced longitudinal rows of staple drivers 330a, 330b, 370a, and 370b as shown in FIG. 11. The "first" inside staple drivers 330a are slidably mounted within corresponding channels 320b and 320c such that each driver 330a supports two staples 222, one in a channel 320b and one in a channel 320c. Likewise, the "second" inside drivers 330b are slidably mounted within channels 320d and 320e such that each driver 330b supports two staples 222, one in a channel 320d and one in a channel 320e. The "outside" drivers 370a and 370b are slidably mounted within the staple-receiving channels 320a and 320f, respectively. Each of the outside drivers 370a and 370b supports a single staple 222. Drivers 370a are referred to herein as "first" outside drivers and drivers 370b are referred to herein as "second" outside drivers.

Figure 12:
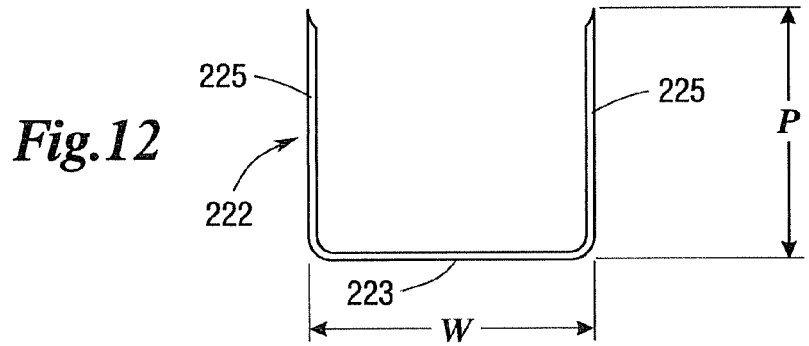
FIG. 12 is a side view of a staple that may be employed with various embodiments of the present invention.

FIG. 12 illustrates a staple 222 that may be used in connection with the various embodiments of the present invention. The staple 222 includes a main portion 223 and two prongs 225. The prongs 225 each have a length "P" and the main portion has a width "W". The reader will appreciate that a variety of different types of staples may be employed. For example, for a vascular staple, "P" may be approximately 0.102 inches; for a regular staple, "P" may be approximately 0.134 inches; and for a thick tissue staple, "P" may be approximately 0.160 inches. For all such staples, "W" may be approximately 0.120 inches. Other sizes of staples 222 may be employed in the manners discussed below.

The inside staple drivers 330a located on one side of the elongated slot 310 are referred to herein as "first" inside staple drivers and the inside staple drivers 330b located on the other side of the elongated slot 310 are referred to herein as "second" inside staple drivers. As will be discussed in further detail below, in one embodiment, the second inside staple drivers 330b are identical to the first inside staple drivers 330a, except for their orientation in their respective channels in the cartridge body 302.

Figure 14:
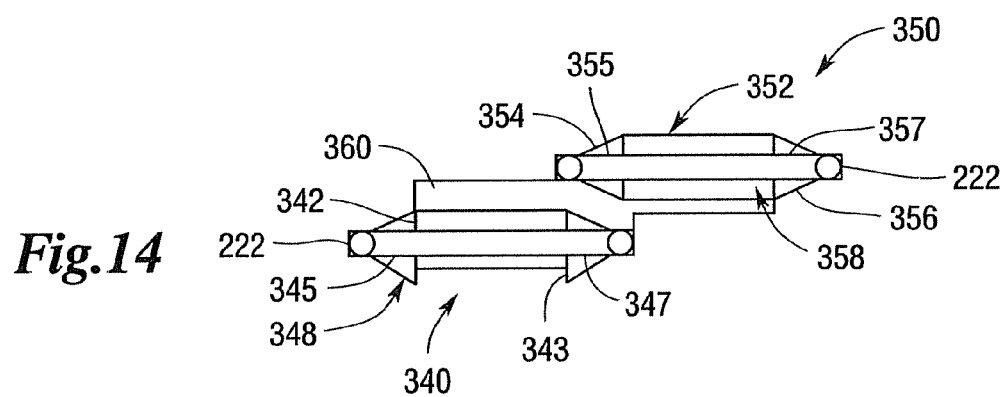
FIG. 14 is a top view of the inside double driver and staples of FIG. 13.
Figure 13:
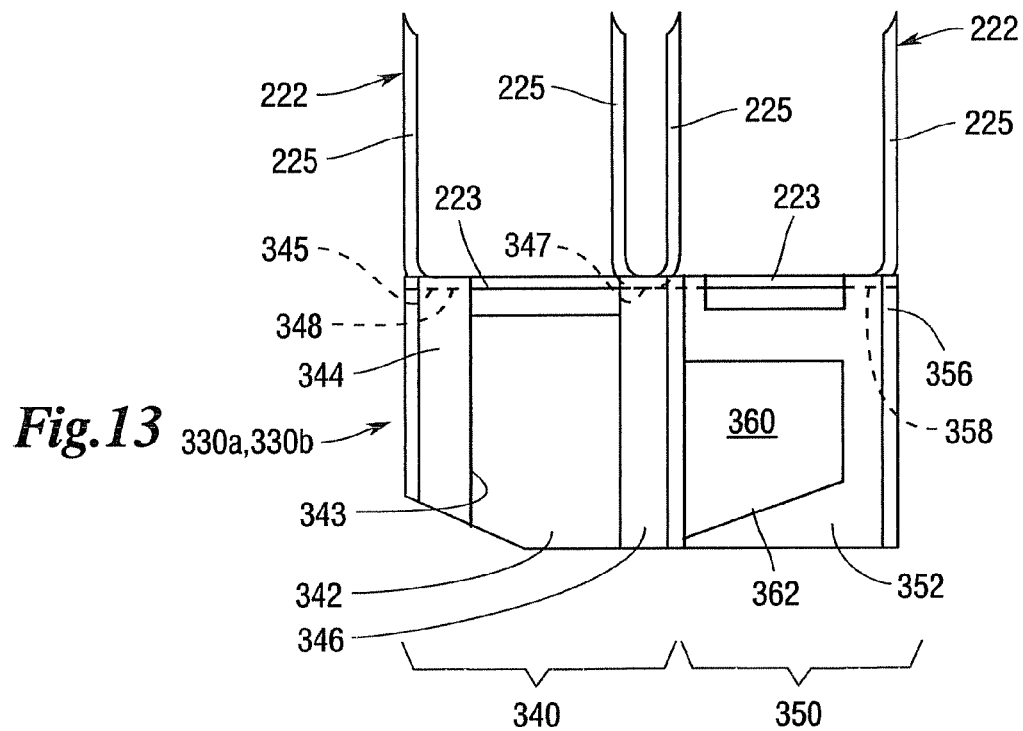
FIG. 13 is a front elevational view of one inside double driver of one embodiment of the present invention supporting two staples thereon.
Figure 15:
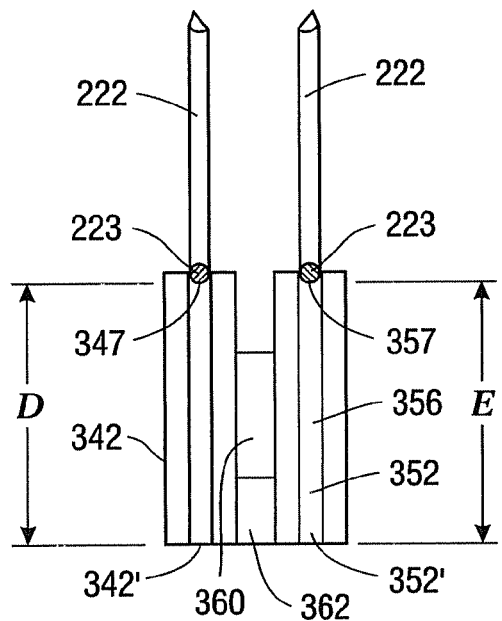
FIG. 15 is a right side elevational view of the inside double driver and staples of FIGS. 13 and 14.

FIGS. 13-15 illustrate one embodiment of a "first" inside double driver 330a for supporting and driving staples 222. As can be seen in those Figures, the staple driver 330a has a primary driver portion 340 and a secondary driver portion 350 that is connected to the first primary portion 340 by a central base member 360. The primary driver portion 340 has a primary driver base 342 that has a groove 343 therein adapted to mate with a corresponding vertically extending tongue (not shown) in the cartridge body 302 for guiding and stabilizing the driver 330a as it moves within its respective channel. The primary driver portion 340 further has a first forward support column 344 and a first rearward support column 346 protruding upward from the first driver base 342. The first forward support column 344 has a first forward staple-receiving groove 345 therein and the first rearward support column 346 has a first rearwardly staple-receiving groove 347 therein. See FIGS. 13-15. The first forward support column 344 and the first rearward support column 346 are spaced from each other and collectively form a first staple cradle 348 for supporting the main portion 223 of the staple 222 therein.

Similarly, the secondary driver portion 350 has a secondary driver base 352 and a secondary forward support column 354 and a secondary rearward support column 356 protruding out from the second driver base 352. The secondary forward support column 354 has a secondary forward staple-receiving groove 355 therein and the secondary rearward support column 356 has a secondary rearward staple-receiving groove 357 therein. The secondary forward support column 354 and the secondary rearward support column 356 are spaced from each other and collectively form a secondary staple cradle 358 for supporting the main portion 223 of another staple 222 therein.

As can be seen in FIGS. 13 and 15, the central base member 360 has an angled rearwardly facing edge 362 adapted to be engaged by a corresponding sled cam as will be discussed in further detail below. As can be seen in FIGS. 13 and 14, in this embodiment, the secondary forward support column 354 of the secondary driver portion is oriented relative to the first rearward support column 346 such that the staple 222 that is supported in the secondary staple cradle 358 is longitudinally offset from the staple 222 in the first staple cradle 348.

The reader will appreciate that the first inside drivers 330a are each installed in one orientation into a corresponding pair of channels 320b and 320c located on one side of the elongated slot 310 in the cartridge body 302. The second inside staple drivers 330b (located on the opposite side of the elongated slot 310 from the first inside staple drivers 330a) comprise inside drivers 330a rotated 180 degrees so that their respective angled surfaces 363 face towards the proximal end 304 of the cartridge 300 to enable them to be installed in pairs of corresponding channels 320d and 320e. Thus, in this embodiment, only one inside driver configuration is employed which thereby eliminates the need for two different inside staple driver configurations for channels on each side of the elongated slot 310.

Figure 17:
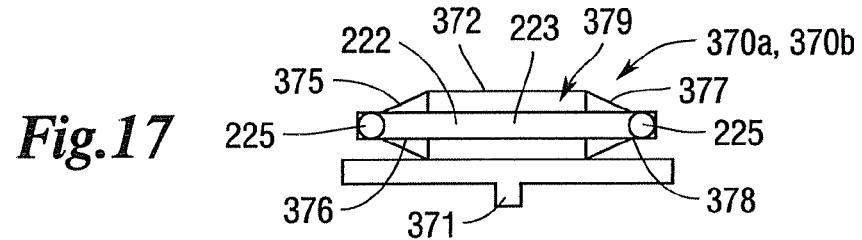
FIG. 17 is a top view of the outside single driver and staple of FIG. 16.
Figure 16:
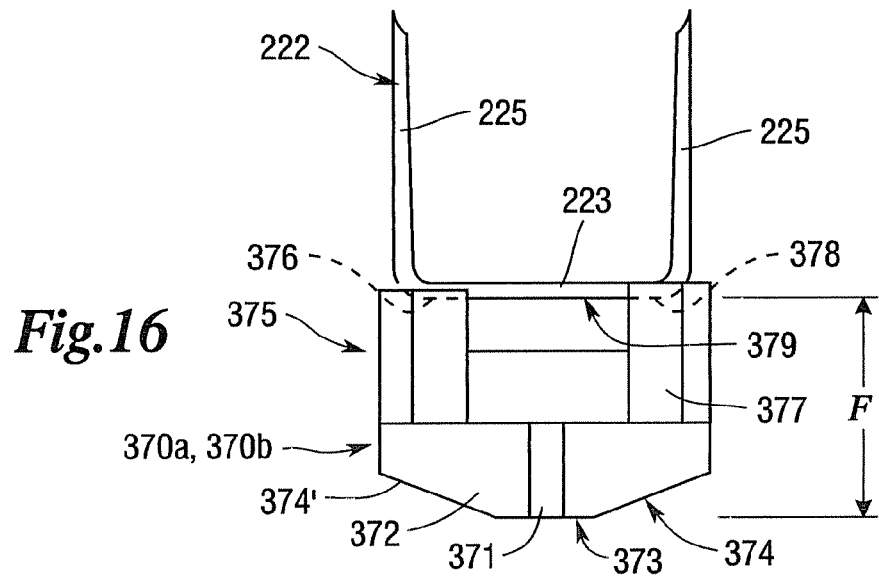
FIG. 16 is a front elevational view of one outside single driver of one embodiment of the present invention supporting a staple thereon.

FIGS. 16 and 17 illustrate one embodiment of a "first" outside staple driver 370a. As can be seen in those FIGS., a first outside staple driver 370a has a second base 372 that has an angled rearwardly facing portion 374. Protruding upward from the second base 372 is a second forward support column 375 that has a second forward staple-receiving groove 376 therein. A second rearward support column 377 also protrudes upward from the second base 372 in a spaced-apart relationship with respect to the second forward support column 375. The second rearward support column 377 has a second rearward staple-receiving groove 378 therein. The support columns 375, 377 collectively form a second staple cradle 379 that is configured to support a staple 222 therein as illustrated in FIGS. 16 and 17. The staple drivers 370a also have a laterally protruding rib 371 which is received in a corresponding groove (not shown) in the cartridge body 302 for guiding and stabilizing the driver 370a as it moves within its respective channel.

The reader will appreciate that a first outside driver 370a is installed in one orientation into a corresponding channel 320a on one side of the elongated slot 310. A second outside staple driver 370b (to be located on the opposite side of the elongated slot 310 from the first outside staple drivers 370a) comprises an outside driver 370a rotated 180 degrees so that the angled surface 374' thereon faces toward the proximal end 304 of the cartridge 300 to enable it to be installed in a corresponding channel 320f in the cartridge body 302. Thus, in this embodiment, only one outside staple driver configuration is employed which avoids the need for two different outside staple driver configurations for channels on each side of the elongated slot 310.

Figure 19:
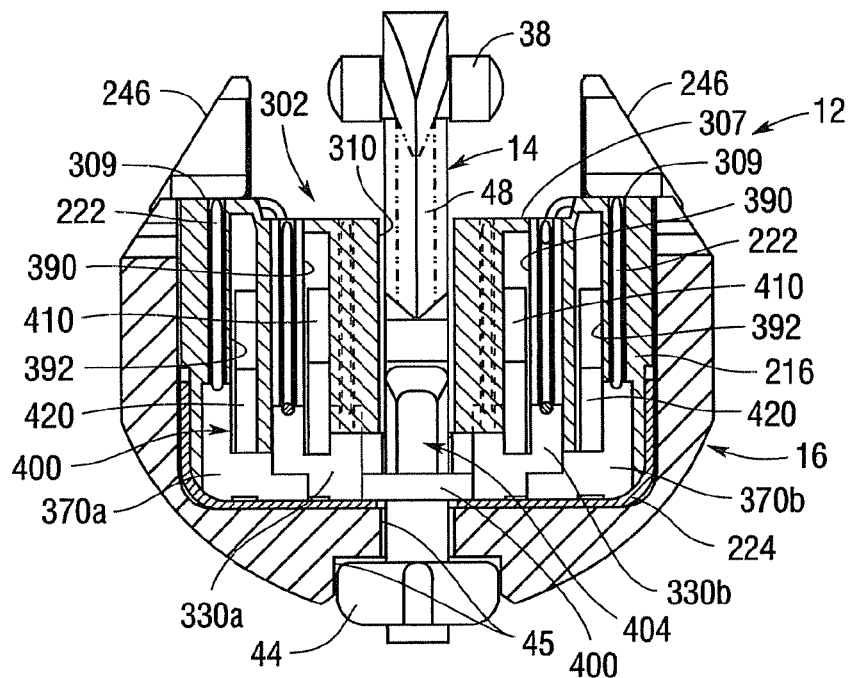
FIG. 19 is a section view taken along line 19-19 of FIG. 10 showing the cross-sectional relationship between the firing bar, elongate channel, wedge sled, staple drivers, staples and staple cartridge.
Figure 19A:
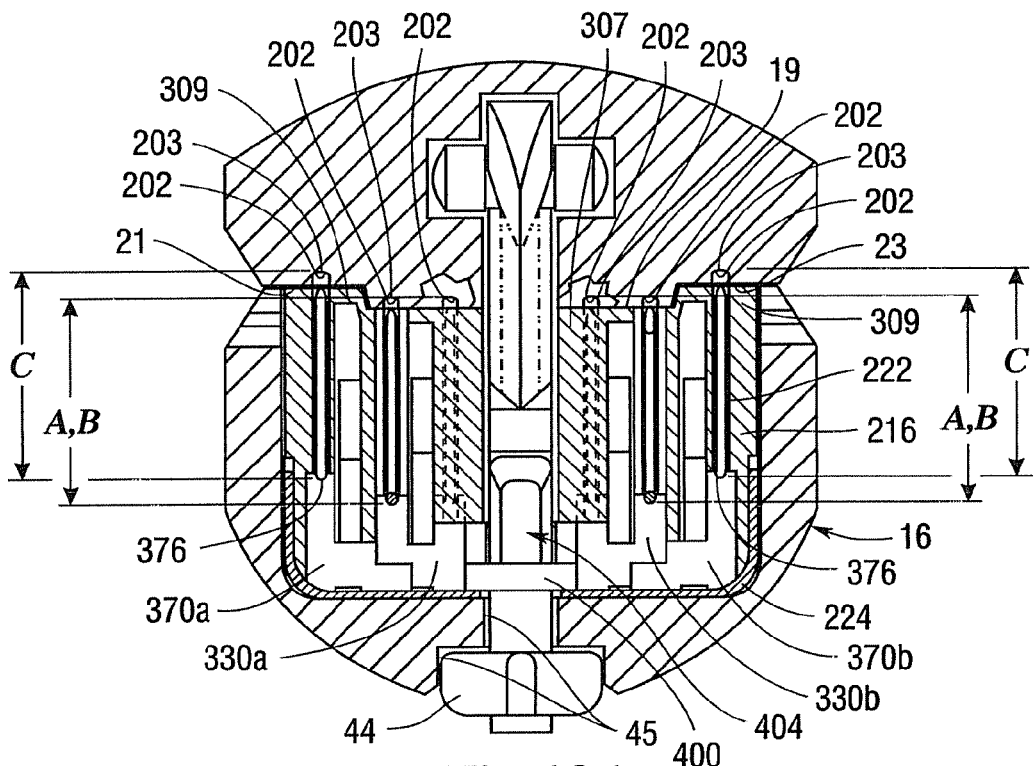
FIG. 19A is another cross-sectional view of an end effector embodiment of the present invention showing the cross-sectional relationship between the firing bar, elongate channel, wedge sled, staple drivers, staples, staple cartridge and anvil.

FIGS. 19 and 19A illustrate in cross-section one embodiment of a staple cartridge of the present invention mounted within one type of end effector 12. The end effector 12 in this embodiment employs a "stepped" anvil 18 of the type illustrated in FIGS. 23-25. In other embodiments, however, the bottom surface of the anvil is planar and not stepped. Others can be seen in FIGS. 19A, and 23-25, the anvil 18 has a central portion 19 that is offset or not coplanar with the two lateral side portions 21, 23. Accordingly, in this embodiment, the upper surface 306 of the cartridge 300 is provided with a recessed central portion 307 and two lateral side portions 309 that are adapted to closely mate with the corresponding portions 19, 21, 23, respectively, of the anvil 18, when the anvil 18 is in the closed position. See FIG. 19A.

Figure 14A:
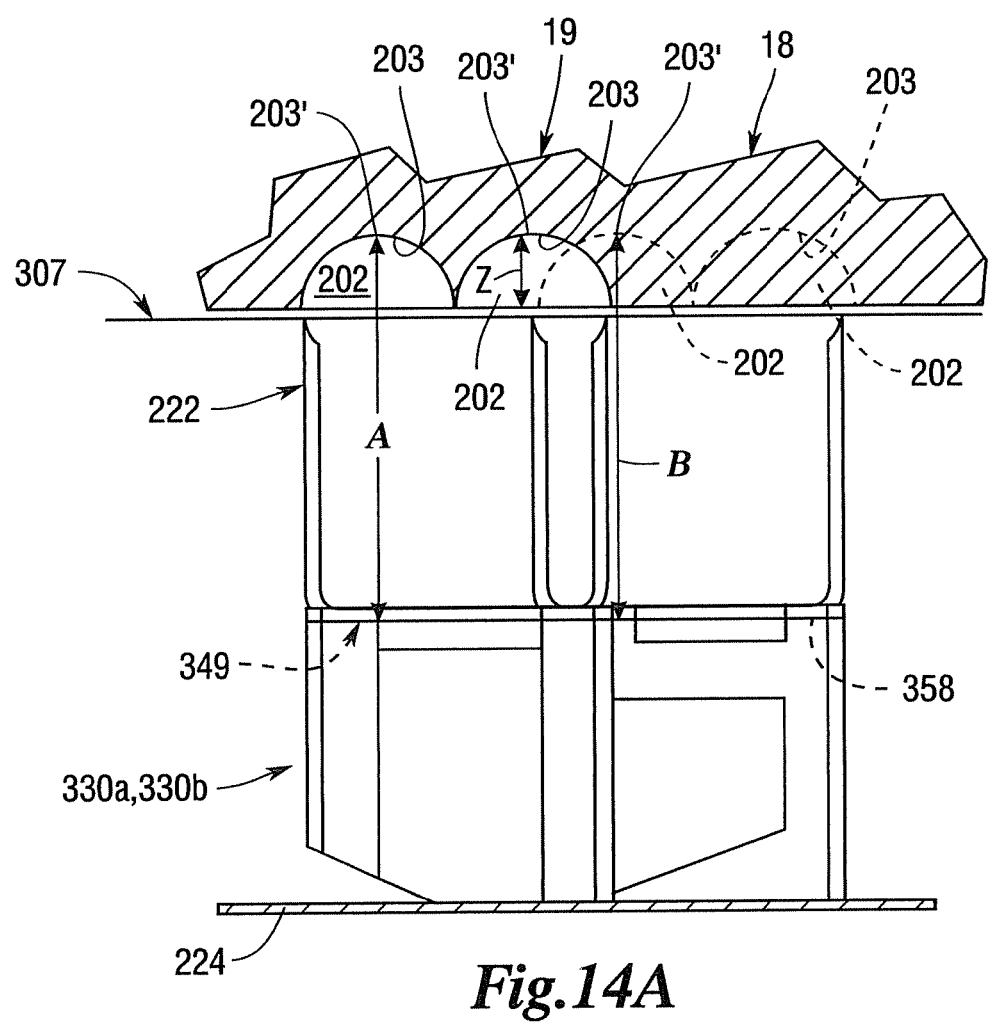
FIG. 14A is an elevational view of the inside double driver of FIG. 13 within a portion of a staple cartridge mounted in the end effector and also illustrating a corresponding portion of the anvil when in a closed position.
Figure 24:
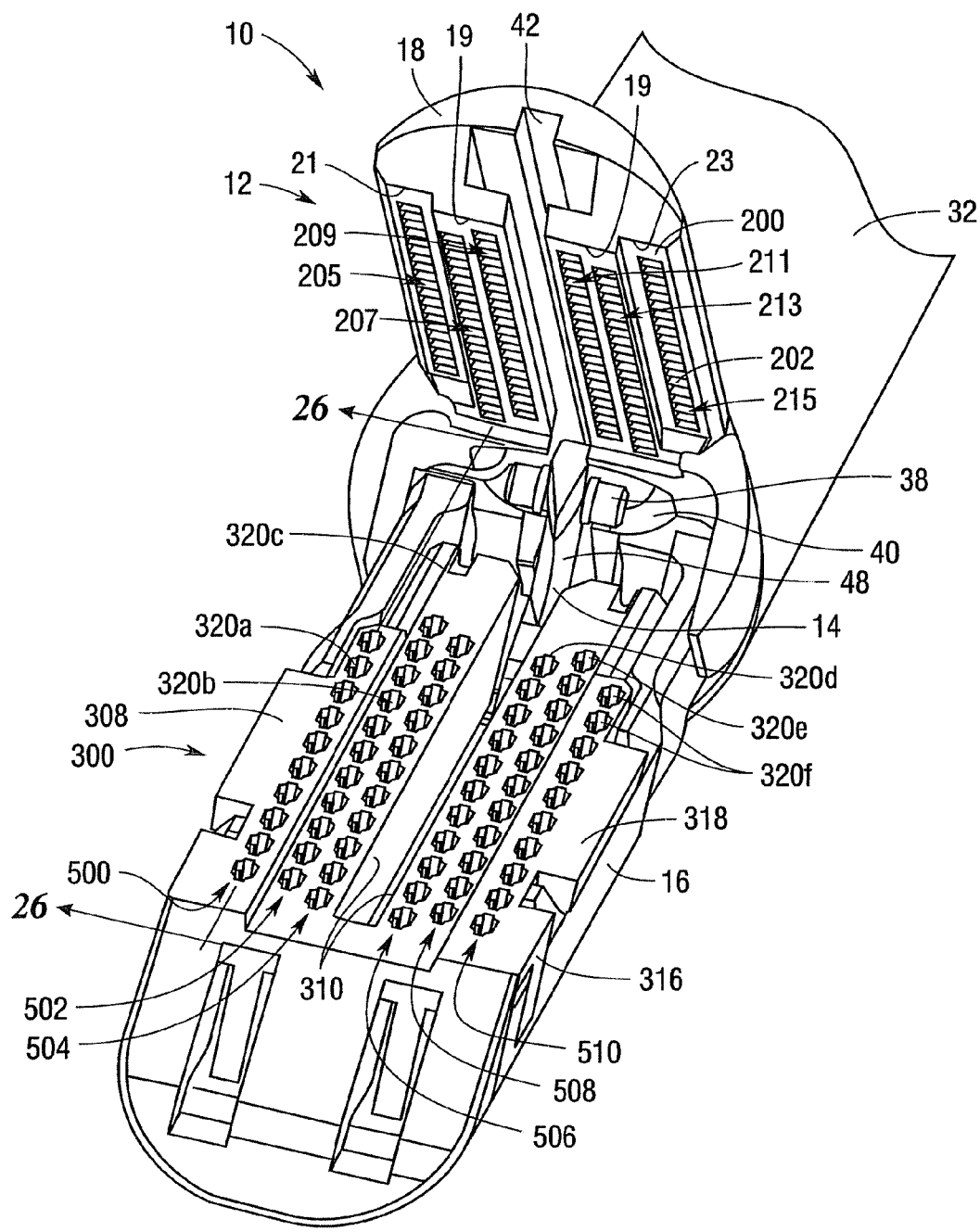
FIG. 24 is an isometric view of the end effector at the distal end of the surgical stapling and severing instrument of FIG. 1 with the anvil in the up or open position exposing the staple cartridge and cutting edge of the firing bar.

As can be seen in FIG. 24, in this embodiment, the under surfaces 200 of anvil 18 are provided with a series of forming pockets 202 that may be arranged in rows that correspond to the rows of channels in the cartridge 300. That is, row 205 of pockets 202 may correspond to channel row 500. Row 207 of pockets may correspond to channel row 502. Row 209 of pockets 202 may correspond to channel row 504. Row 211 of pockets 202 may correspond to channel row 506. Row 213 of pockets 202 may correspond to channel row 508. Row 215 of pockets 202 may correspond to channel row 510. Each pocket 202 has at least one forming surface 203 therein that is adapted to contact the ends of the staple prongs 225 being driven therein to thereby cause the prongs 225 to bend inwardly toward each other. In one embodiment, each pocket 202 has two intersecting arcuate forming surfaces 203 that are oriented as shown in FIG. 14A. Each arcuate forming surface has an apex 203' that defines a maximum pocket depth "Z". However other forming pocket configurations could be employed.

Returning to FIGS. 18 and 19, it can be seen that in one embodiment, the cartridge body 302 is mounted within the cartridge tray 224. As illustrated in FIG. 19, the cartridge body 302 is formed with two inside longitudinally extending slots 390 and two outside longitudinally extending slots 392. Slots 390 and 392 extend from the proximal end 304 of the cartridge to its tapered outer tip 306 (shown in FIG. 10). This embodiment further includes a wedge sled 400 that slidably supported on the cartridge tray 224. One wedge sled embodiment 400 includes a pair of inside sled cams 410, wherein one inside sled cam 410 corresponds to one of the inside longitudinally extending slots 390 and wherein the other inside sled cam 410 corresponds to the other inside longitudinally extending slot 390. See FIG. 19. The wedge sled 400 further includes a pair of outside sled cams 420, wherein one outside sled cam 420 corresponds to one of the outside longitudinally extending slots 392 and the other outside sled cam 420 corresponds to the other outside longitudinally extending slot 392 as shown in FIG. 19. When assembled, the cartridge tray 224 holds the wedge sled 400 and the drivers 330a, 330b, 370a, 370b inside the cartridge body 302.

Figure 18:
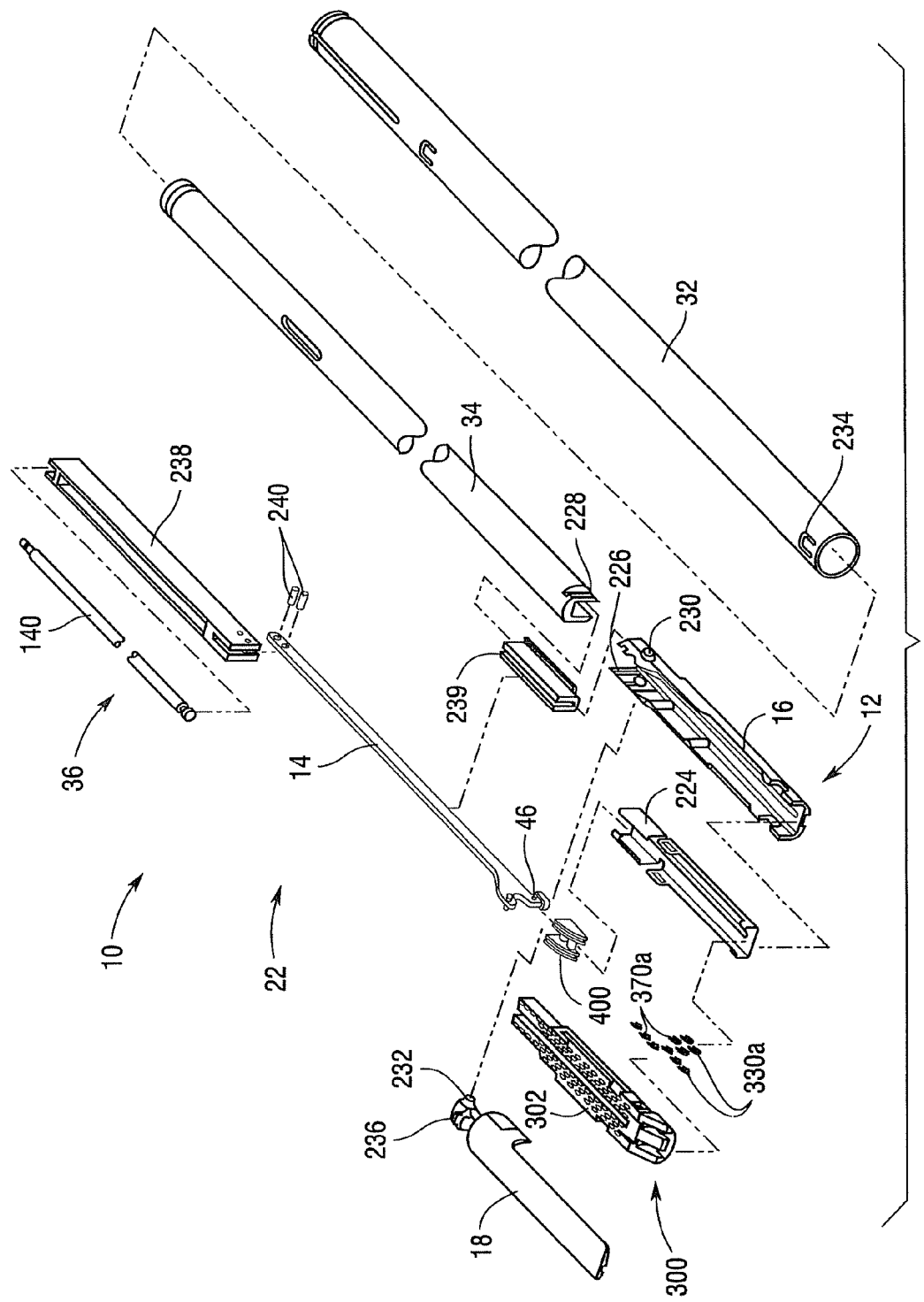
FIG. 18 is an isometric exploded view of the implement portion of the surgical stapling and severing instrument of FIG. 1.

As can be seen in FIG. 18, the elongate channel 16 has a proximally placed attachment cavity 226 that receives a channel anchoring member 228 on the distal end of the frame 34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 20:
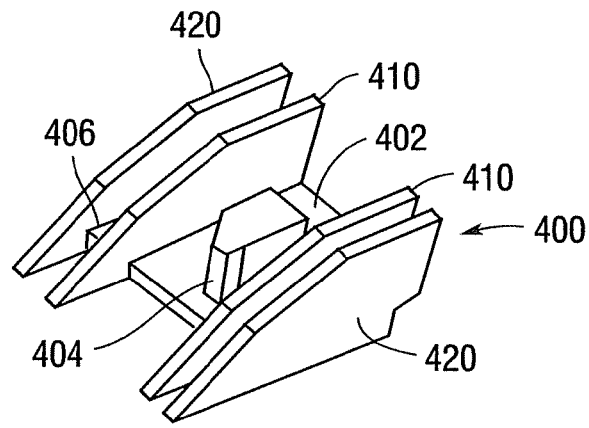
FIG. 20 is a perspective view of one wedge sled embodiment of the present invention.
Figure 21:
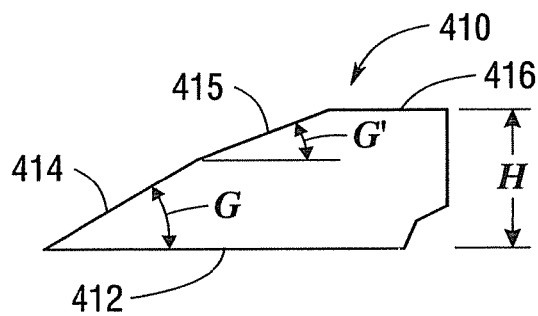
FIG. 21 is a side elevational view of an inside sled cam of the wedge sled depicted in FIG. 20.
Figure 22:
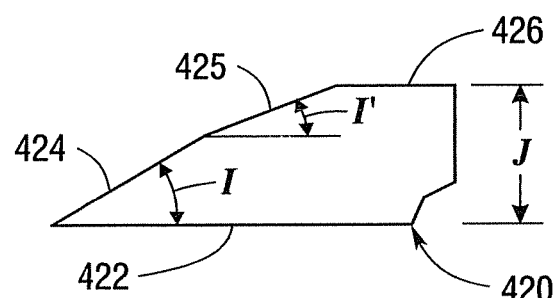
FIG. 22 is a side elevational view of an outside sled cam of the wedge sled depicted in FIG. 20.
Figure 23:
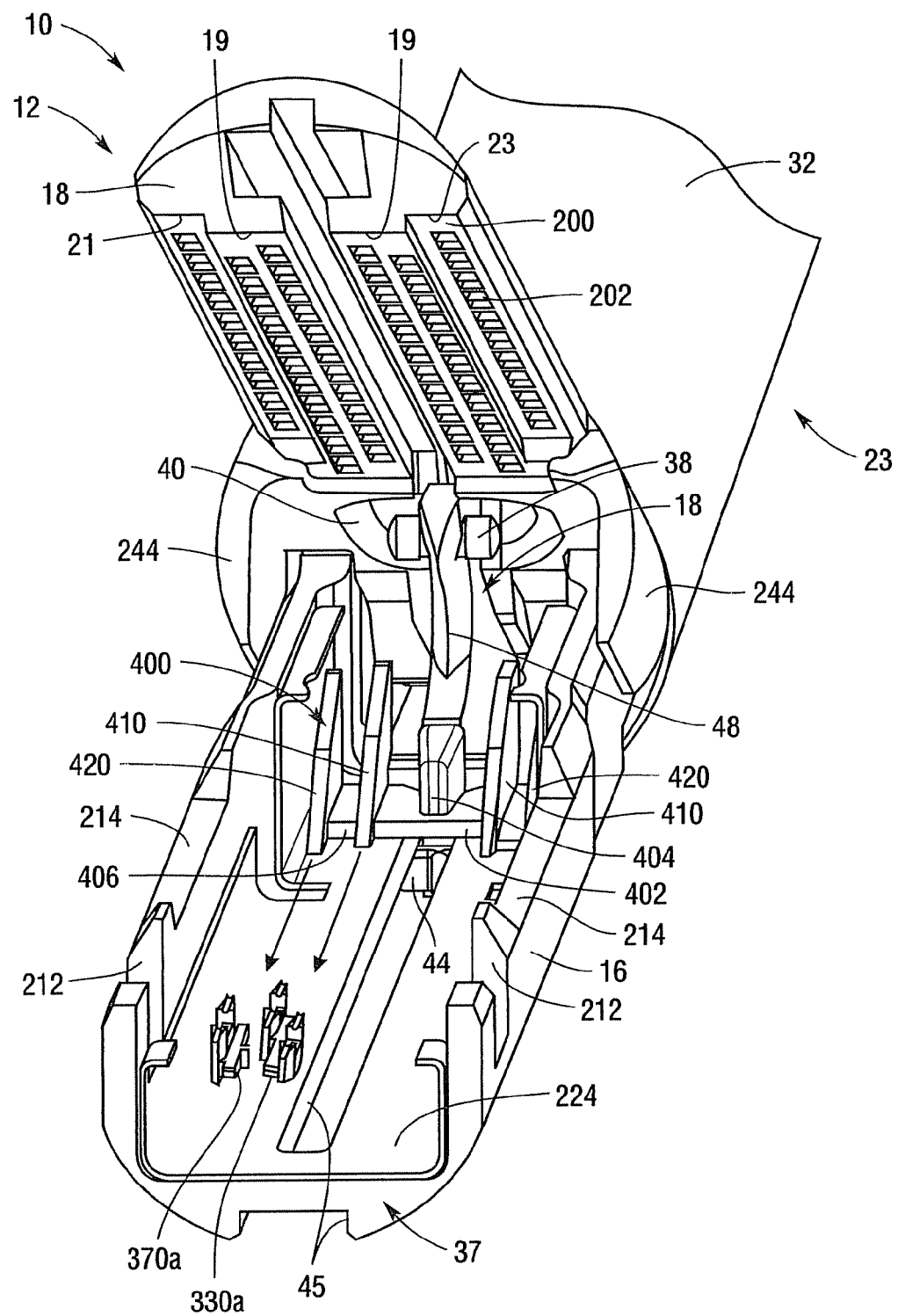
FIG. 23 is an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar.

FIGS. 20-23 illustrate one embodiment of the wedge sled 400 of the present invention. As can be seen in FIGS. 20 and 23, the wedge sled 400 includes a central spacer portion 402 that extends between the inside sled cams 410. A pusher block 404 is formed on the central spacer portion 402 for engagement with the middle pin 46 of the firing bar 14. A side profile of one embodiment of an inside sled cam 410 is depicted in FIG. 21. As can be seen in that FIG., the inside sled cam 410 has a bottom surface 412, and a first camming surface 414 that forms an angle "G" with the bottom surface 412 and a second camming surface 415 that extends to a top surface 416. In one embodiment, for example, the angle "G" may be 35 degrees and the angle "G" may be 20 degrees. The height of the inside sled cam 410 (the distance between the bottom surface 412 and the top surface 416) is represented as "first" sled cam height "H". In one embodiment, distance "H' is approximately 0.173 inches and the length of the top surface 416 may vary from embodiment to embodiment. As will be further evident as the present Detailed Description proceeds, the first sled cam height represents the vertical distance that the inside sled cams 410 will drive the corresponding inside drivers 330a, 330b toward the anvil 18 during operation.

The wedge sled 400 further comprises lateral spacer portions 406 that extend between the inside sled cams 410 and the outside sled cams 420 as shown in FIGS. 20 and 23. A side profile of one embodiment of an outside sled cam 420 is depicted in FIG. 22. In this embodiment, the outside sled cam 420 has a bottom surface 422 and a first camming surface 424 that forms an angle "I" with respect to the bottom surface 422 and a second camming surface 425 that to a top surface 426. In one embodiment, angle "I" may be approximately 35 degrees and angle "I" may be approximately 20 degrees. The height of the outside sled cam 420 (the distance between the bottom surface 412 and the top surface 416) is represented as the "second" sled cam height "J". In one embodiment, distance "J' is approximately 0.163 inches. The second sled cam height represents the vertical distance that the outside sled cams 420 will drive the corresponding outside drivers 370a, 370b toward the anvil 18 during operation. The reader will understand that the above-recited dimensions are illustrative of one embodiment and may vary for other embodiments.

With particular reference to FIG. 23, a portion of the staple cartridge 300 is removed to expose portions of the elongate channel 16, such as recesses 212, 214 and to expose some components of the staple cartridge 300 in their unfired position. In particular, the cartridge body 302 (shown in FIG. 18) has been removed. The wedge sled 400 is shown at its proximal, unfired position with a pusher block 404 contacting the middle pin 46 (not shown in FIG. 23) of the firing bar 14. The wedge sled 400 is in longitudinal sliding contact upon the cartridge tray 224 and includes wedges sled cams 410, 420 that force upward the double drivers 330a, 330b and the single drivers 370b, 370b as the wedge sled 400 moves distally. Staples 222 (not shown in FIG. 23) resting upon the drivers 330a, 330b, 370a, 370b are thus also forced upward into contact with the anvil forming pockets 202 in anvil 18 to form closed staples. Also depicted is the channel slot 45 in the elongate channel 16 that is aligned with the elongated slot 310 in the staple cartridge 300.

FIG. 24 depicts the end effector 12, which is in an open position by a refracted closure sleeve 32, with a staple cartridge 300 installed in the elongate channel 16. The firing bar 14 is at its proximal position, with the upper pin 38 aligned in a non-interfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 300, thereby allowing removal of a spent cartridge and insertion of an unfired cartridge, which may be "snapfit" into the elongate channel 16. Specifically, in this embodiment, extension features 316, 318 of the staple cartridge 300 engage recesses 212, 214, respectively (shown in FIG. 23) of the elongate channel 16.

Figure 25:
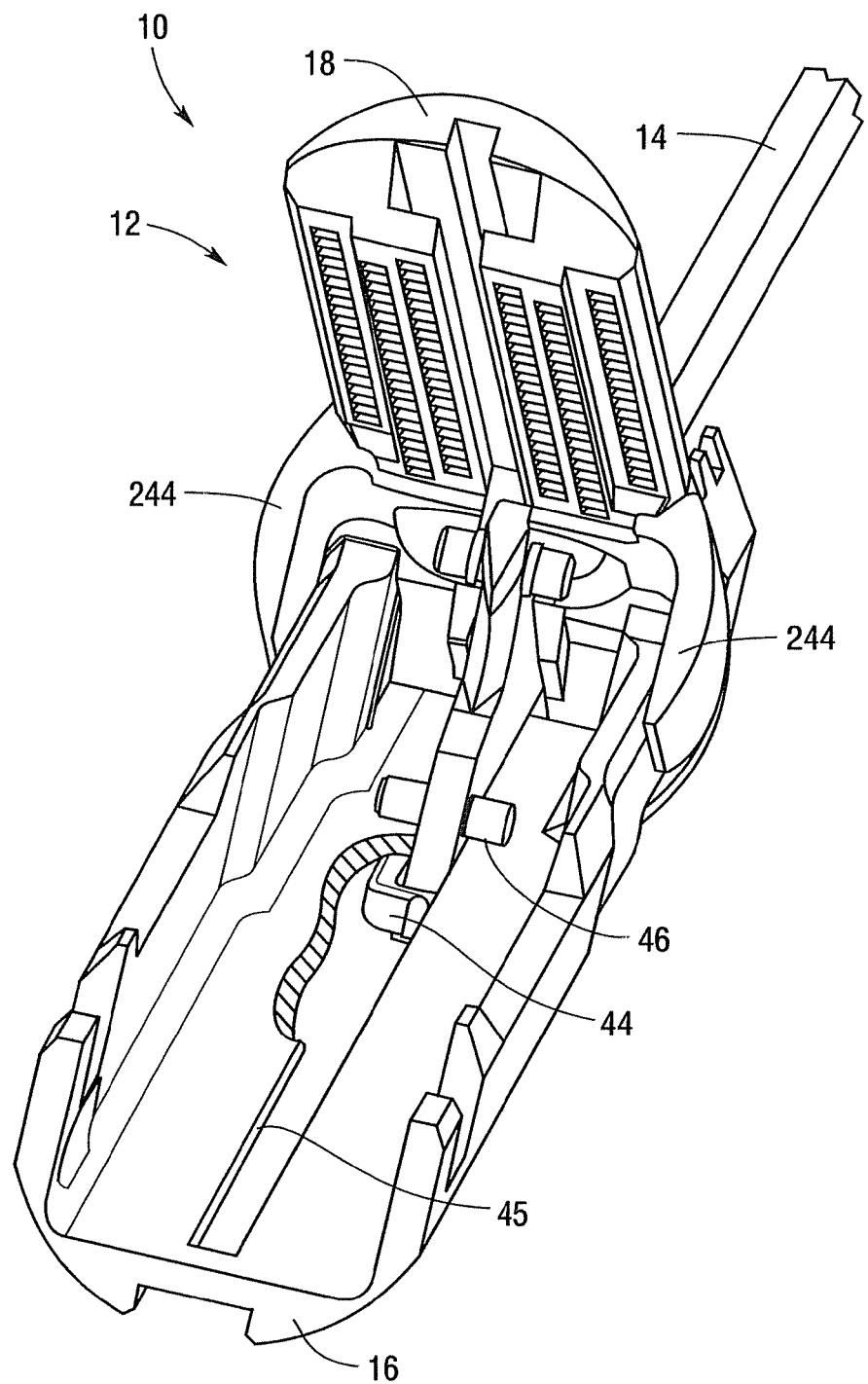
FIG. 25 is an isometric view of the distal end of the surgical stapling and severing instrument of FIG. 1 with the anvil in the up or open position with the staple cartridge completely removed and a portion of an elongate channel removed to expose a lowermost pin of the firing bar.

FIG. 25 depicts the end effector 12 of FIG. 23 with all of the staple cartridge 300 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot is a pair of opposing tissue stops 244 which serve to prevent tissue from being positioned too far up into the end effector 12 during clamping.

Figure 26:
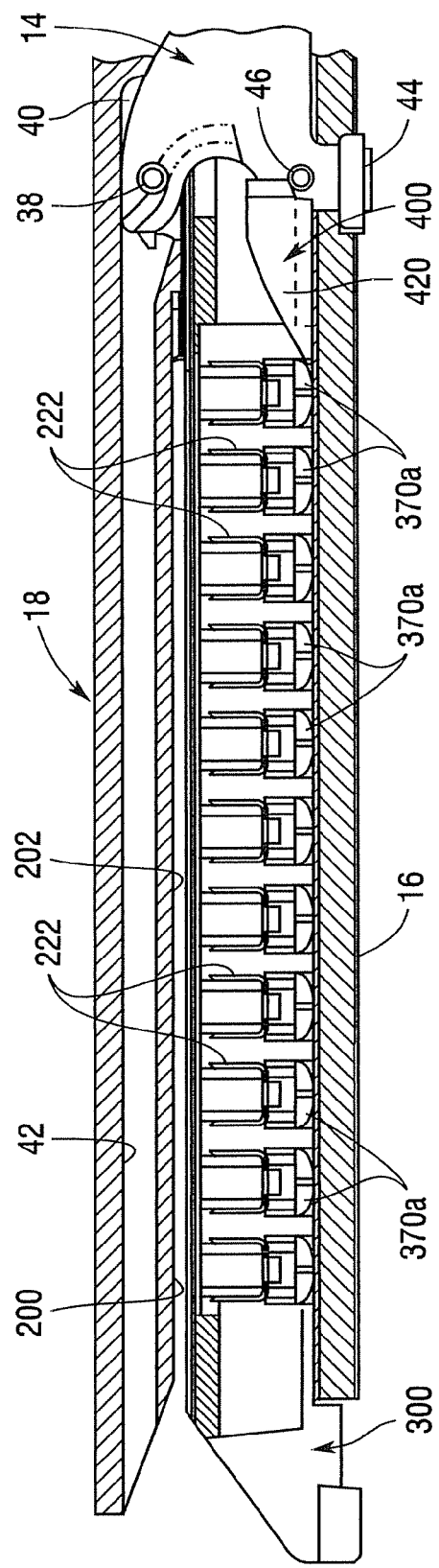
FIG. 26 is a side elevation view in section showing a mechanical relationship between the anvil, elongate channel, and staple cartridge in the closed position of the surgical stapling and severing instrument of FIG. 1, the section generally taken along lines 26-26 of FIG. 24 to expose wedge sled, staple drivers and staples but also depicting the firing bar along the longitudinal centerline.

FIG. 26 depicts the end effector 12 in a closed position with the firing bar 14 in an unfired position. The upper pin 38 is in the anvil pocket 40 and is vertically aligned with the anvil slot 42 for distal longitudinal movement of the firing bar 14 during firing. The middle pin 46 is positioned to push the wedge sled 400 distally so that the sled cams 410, 420 contact and lift double drivers 330a, 330b and the single drivers 370a, 370b, respectively, to drive them upwardly toward the anvil 18.

Figure 15A:
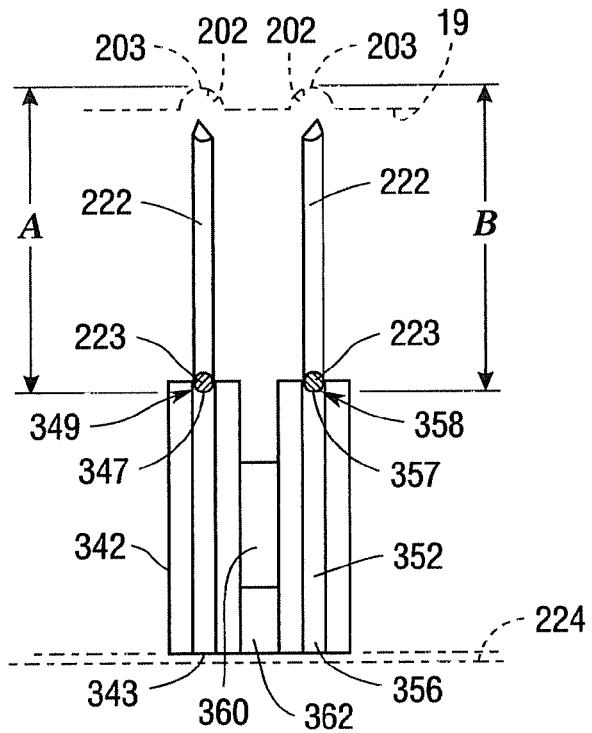
FIG. 15A is another side elevational view of the inside double driver of FIG. 15 wherein corresponding portions of the cartridge tray and anvil are illustrated in broken lines to depict the relationships therebetween.

As can be appreciated from reference to FIGS. 14A, 15A and 19A, in one embodiment of the present invention, the distance between the bottom of the first staple-receiving grooves 345, 347 forming the first staple cradle 349 and the apex 203' of forming surfaces 203 of the corresponding forming pocket 202 of anvil 18, when the anvil 18 is in the closed position and when the inside driver 330a, 330b is supported on the cartridge tray 224, is referred to herein as the first staple forming distance "A". The distance between the bottom of the secondary staple-receiving grooves 345, 347 forming the secondary staple cradle 349 and the apex 203' of the forming surface 203 of the corresponding forming pocket 202 in the anvil 18 when the anvil 18 is in the closed position and the inside driver 330a, 330b is supported on the cartridge tray 224 is referred to herein as the secondary staple forming distance "B". In one embodiment, the first staple forming distance "A" and the secondary staple forming distance "B" are substantially equal to each other. In other embodiments, those distances "A" and "B" may differ from each other.

Figure 16A:
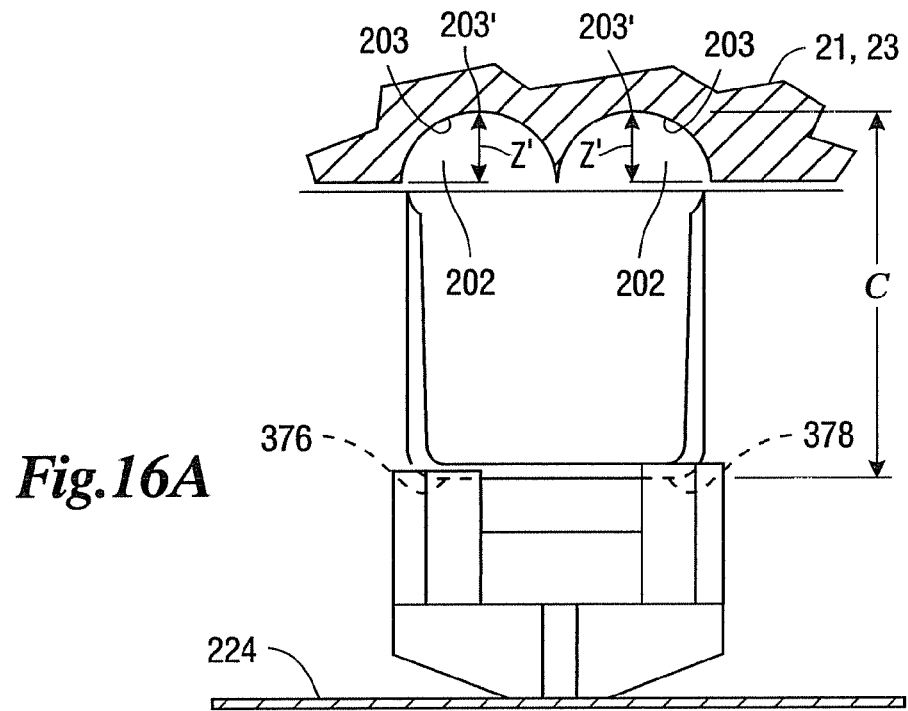
FIG. 16A is another front view of the outside single driver of FIG. 16 with portions of the cartridge tray and anvil shown to illustrate the relationships therebetween.

As illustrated in FIGS. 16A and 19A the distance between the bottom of the second staple-receiving grooves 376, 378 that form the second staple cradle 379 and the apex 203' of the forming surface 203 of a corresponding forming pocket 202 in anvil 18 when the anvil 18 is in the closed position and the outside drivers 370a, 370b are supported on the cartridge channel 224, is referred to herein as a "second" staple forming distance "C".

Figure 27:
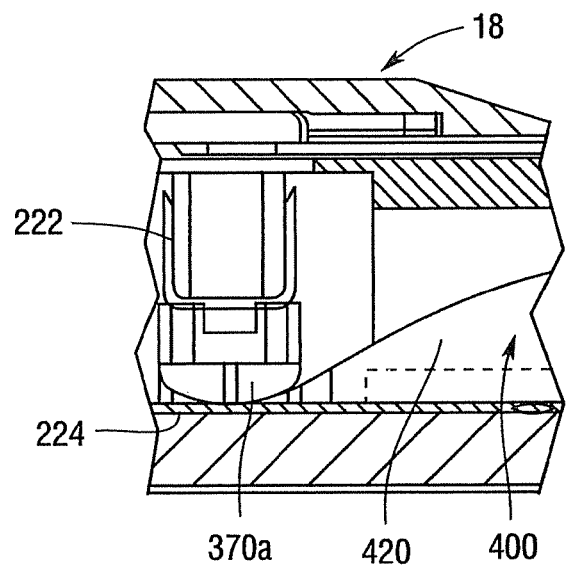
FIG. 27 is a cross-sectional view of a portion of one embodiment of a staple cartridge of the present invention wherein an outside cam of a wedge is adjacent to an outside single driver.
Figure 28:
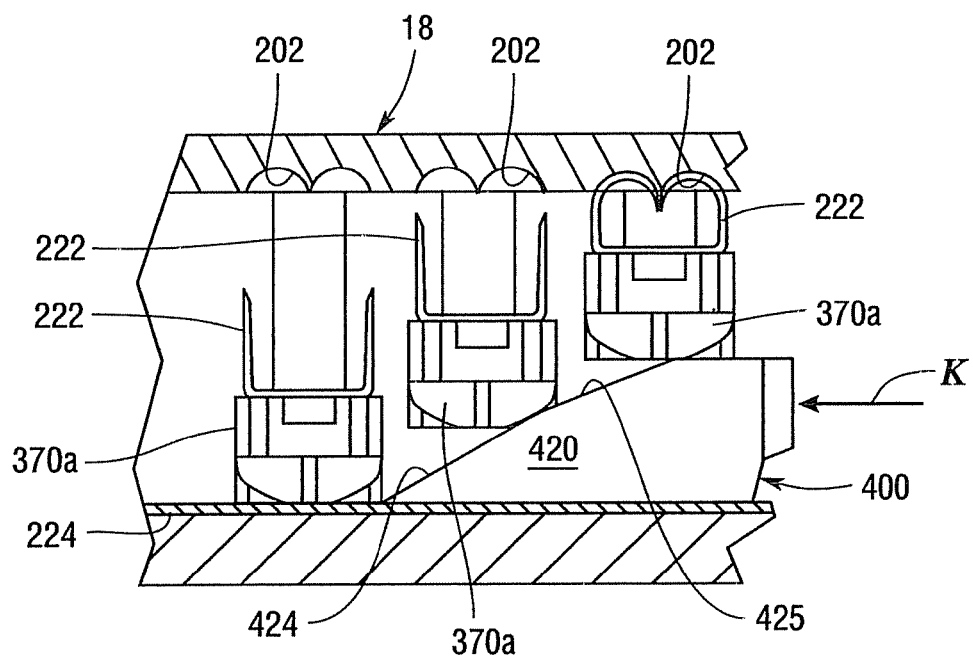
FIG. 28 is a cross-sectional view of a portion of one embodiment of a staple cartridge of the present invention wherein an outside cam of a wedge sled is engaging three outside single drivers.

FIGS. 27 and 28 illustrate the forming of staples supported on some of the first outside drivers 370a. In FIG. 27, one of the outside sled cams 420 of the wedge sled 400 is initially contacting one of the outside drivers 370a. As the wedge sled 400 continues in the driving direction represented by arrow "K" in FIG. 28, the outside sled cam 420 causes the outside drivers 370a drive the staples 222 supported thereby into the staple forming pockets 202 in the anvil 18. Likewise, as the wedge sled 400 is driven in the driving direction "K", the inside sled cams 410 contact the inside drivers 330a, 330b and causes them to drive the staples 222 supported thereby into the corresponding staple forming pockets 202 in the anvil 18.

As indicated above, in some applications involving an area of varied tissue composition, it can be desirable to form rows of staples wherein the formed (final) heights of the staples in a row that is the farthest distance away from the cut line are greater than the formed (final) heights of those staples in the row that is closest to the cut line. In other applications, it may be desirable for the formed heights of the staples in a single row to increase (or decrease) from staple to staple. Another clinical benefit would be to have the formed heights of the staples in the outermost rows larger than formed heights of the staples in the inside rows. The various embodiments of the subject invention can provide these results while employing identical staples in all of the rows.

As the present Detailed Description proceeds, those staples 222 in the outermost rows 520, 530 of staples (those staples formed using the outside staple drivers 370a, 370b) will be referred to hereinafter as staples 222' and those staples in the innermost rows 522, 524, 526, 528 of staples (those staples formed using the inside staple drivers 330a, 330b) will be referred to hereinafter as staples 222". It will be understood, however, that staples 222' and 222" are identical to each other prior to being formed by the various embodiments of the present invention. That is, staples 222' and 222" each have identical prong lengths "P" and widths "W".

Returning to FIGS. 14A-16A and 21 and 22, the above desired effects may be attained by altering the staple forming distances "A", "B", and "C" relative to each other and/or the sled cam heights "H" and "J". In one embodiment of the subject invention, for example, the height "H" of each of the inside sled cams 410 is substantially equal to the sled height "J" of each of the outside sled cams 420. See FIGS. 21 and 22. In this embodiment, the staple forming distances "A" and "B" are substantially equal to each other, but distances "A" and "B" are less than the staple forming distance "C". The distance "D" between the bottoms of the first staple-receiving grooves 345, 347 and the bottom surface 342' of the primary driver base 342 is substantially equal to the distance "E" between the bottoms of the secondary staple-receiving grooves 356, 357 and the bottom surface 352' of the secondary driver base portion 352. See FIG. 15. Also in this embodiment, the distance "F" between the bottoms of the second staple-receiving grooves 376 and 378 and the bottom surface 373 of the third base 372 of the outside drivers 370a, 370b (FIG. 16) is less than distances "D" and "E" (FIG. 15). Because the forming distance "C" is greater than the forming distances "A" and "B", the staples 222 supported and formed by the outside drivers 370a, 370b are not compressed as much as the staples supported and formed by the inside drivers 330a, 330b. It will be understood that similar results may be attained on the opposite side of the elongated slot 310 and the cut line 600 formed in the tissue by using the same arrangements and sizes of inside drivers 330b and outside drivers 370b. In an alternative embodiment, the same effect may be achieved by altering the depths of the forming pockets 202 corresponding to the drivers 330a and 370b such that forming distance "C" is greater than the forming distances "A" and "B". That is, the depth (distance "Z" in FIG. 16A) of the forming pockets 202 corresponding to the outside drivers

370*a*. 370*b* may be greater than the depth (distance "Z" in FIG. 14A) of the forming pockets 202 that correspond to the inside drivers 330*a*, 330*b*.

Figure 29:
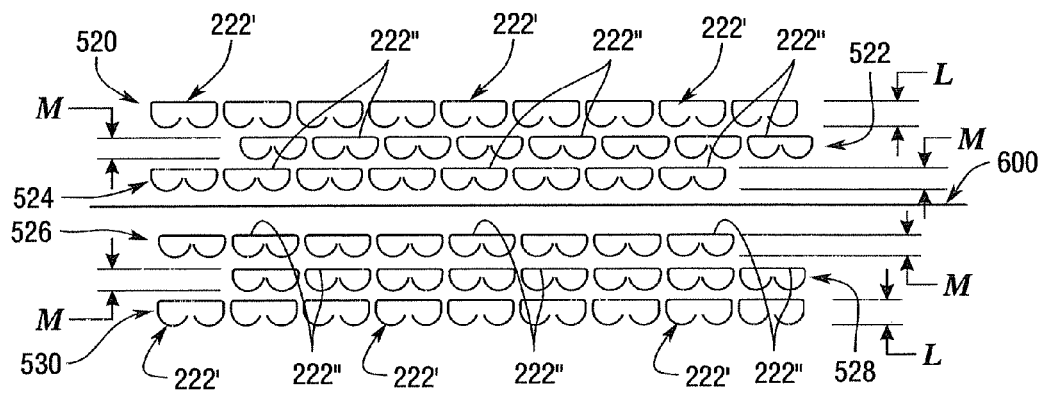
FIG. 29 is a diagrammatic representation of lines of staples installed on each side of a cut line using a surgical stapling and severing instrument of one embodiment of the present invention.
Figure 31:
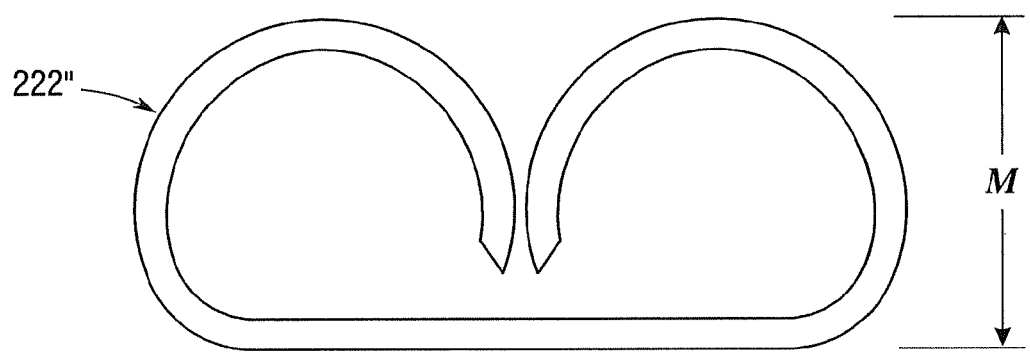
FIG. 31 depicts another staple formed by one outside driver embodiment of the present invention.
Figure 30:
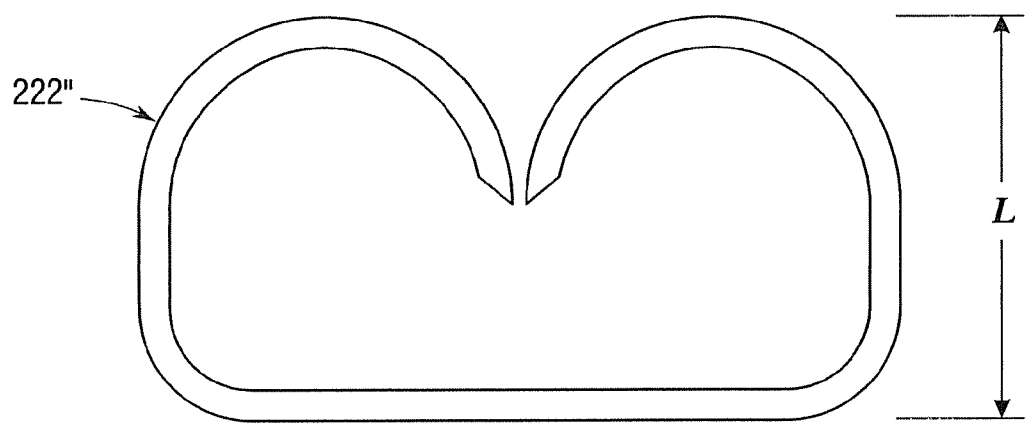
FIG. 30 depicts a staple formed by one inside driver embodiment of the present invention.

FIG. 29 illustrates the rows of staples formed on each side of a cut line 600 utilizing this embodiment of the present invention wherein the forming distances "A" and "B" are equal to each other and the forming distance "C" is greater than the forming distances "A" and "B". For example, if forming distance "C" is 0.020" greater than forming distances "A" and "B", the formed height of the outside staples 222' (represented as dimension "L" in FIG. 30) in rows 520 and 530 would be 0.020 inches is greater than the formed height of the inside staples 222" (represented as dimension "M" in FIG. 31) in rows 522, 524, 526, 528.

The same result may be achieved by utilizing another embodiment of the present invention wherein the forming distances "A", "B" and "C" are essentially equal. In this embodiment, however, the height of each of the inside sled cams 410 (distance "H" in FIG. 21) is greater than the height of each of the outside sled cams 420 (distance "J" in FIG. 22). Thus, because the height "H" of the inside sled cams 410 is greater than the height "J" of the outside sled cams 420, the inside sled cams 410 will drive the corresponding inside drivers 330*a*, 330*b* further towards the anvil than the outside sled cams 420 will drive the corresponding outside drivers 370*a*, 370*b*. Such driving action will cause the staples supported by the inside drivers 330*a*, 330*b* to be compressed to a greater extent than those staples supported by the outside drivers 370*a*, 370*b*. For example, if distance "H" is 0.020 inches greater than distance "J", the formed height of staples 222' in lines 520, 530 would be 0.020" greater than the formed height of staples 222" in lines 522, 524, 526, 528.

Figure 32:
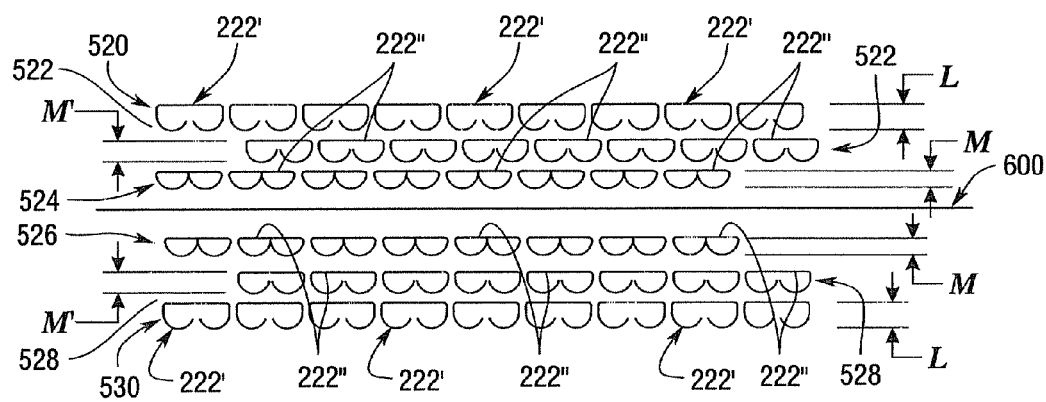
FIG. 32 is a diagrammatic representation of lines of staples installed on each side of a cut line using a surgical stapling and severing instrument of another embodiment of the present invention.

When employing yet another embodiment of the present invention, the outside rows 520, 530 of staples 222' and the inside rows 522, 528 of staples 222" may be formed with heights that are greater than the formed heights of the staples 222" in the inside rows 524, 526. See FIG. 32. This result is achieved by making the forming distances "C" greater than the forming distance "A" and making forming distance "A" greater than secondary forming distance "B".

Figure 33:
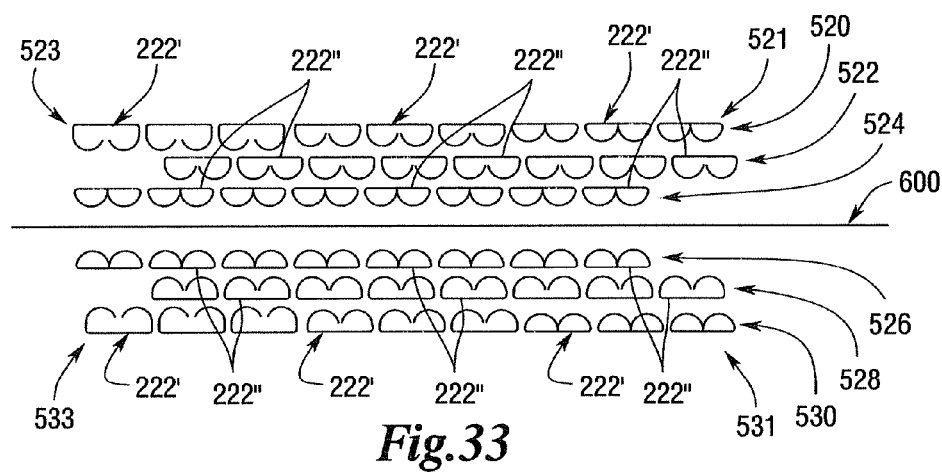
FIG. 33 is a diagrammatic representation of lines of staples installed on each side of a cut line using a surgical stapling and severing instrument of another embodiment of the present invention.
Figure 34:
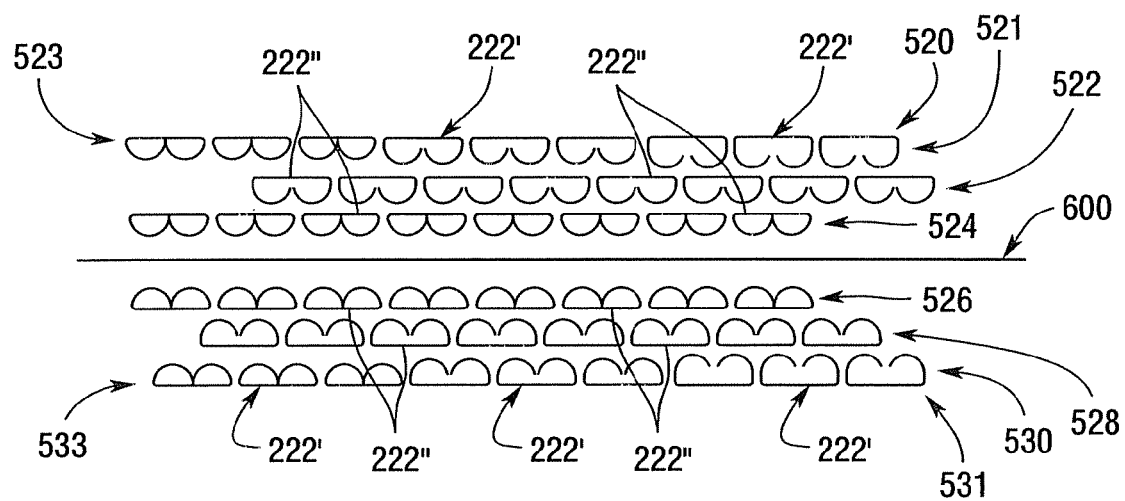
FIG. 34 is a diagrammatic representation of lines of staples installed on each side of a cut line using a surgical stapling and severing instrument of another embodiment of the present invention.

Another embodiment of the present invention can be used to install staples where it is desirable for the formed heights of staples in a single row to vary. One such arrangement is depicted in FIG. 33. As can be seen in FIG. 33, the formed heights of the staples 222' in the outside rows 520, 530 increase when moving from the proximal ends 521, 531 of each row 520, 530, respectively to the distal ends 523, 533 of each row 520, 530, respectively. This effect may be accomplished by decreasing the forming distance "C" for each succeeding driver 370*a*, 370*b*. That is, the driver 370*a* closest the proximal end of the cartridge 300 would be sized to establish a forming distance "C" that is greater than the forming distance "C" achieved by the adjacent driver 370*a* and so on to achieve a condition wherein each succeeding staple 222' (moving in the direction from the proximal end to the distal end of the cartridge 300) would have larger formed heights. This result could also be attained in the staples 222" in rows 522, 524, 526, 528 by similarly altering the forming distances "A" and/or "B" attained by each driver 330*a*, 330*b*. Likewise, formed heights of the staples 222' in the outside rows 520, 530 could be made to decrease when moving from the proximal ends 521, 531 of each row 520, 530, respectively, to the distal ends 523, 533 of each row 520, 530, respectively. This result may be attained by increasing the forming distance of each succeeding driver 370*a*, 370*b*. That is, the driver 370*a* closest the proximal end of the cartridge 300 would have a forming distance "C" that is less than the forming distance "C" of the adjacent driver 370*a* and so on to achieve a condition wherein each succeeding staple 222' (moving in the direction from the proximal end to the distal end of the cartridge) would have smaller formed heights. See FIG. 34.

Figure 35:
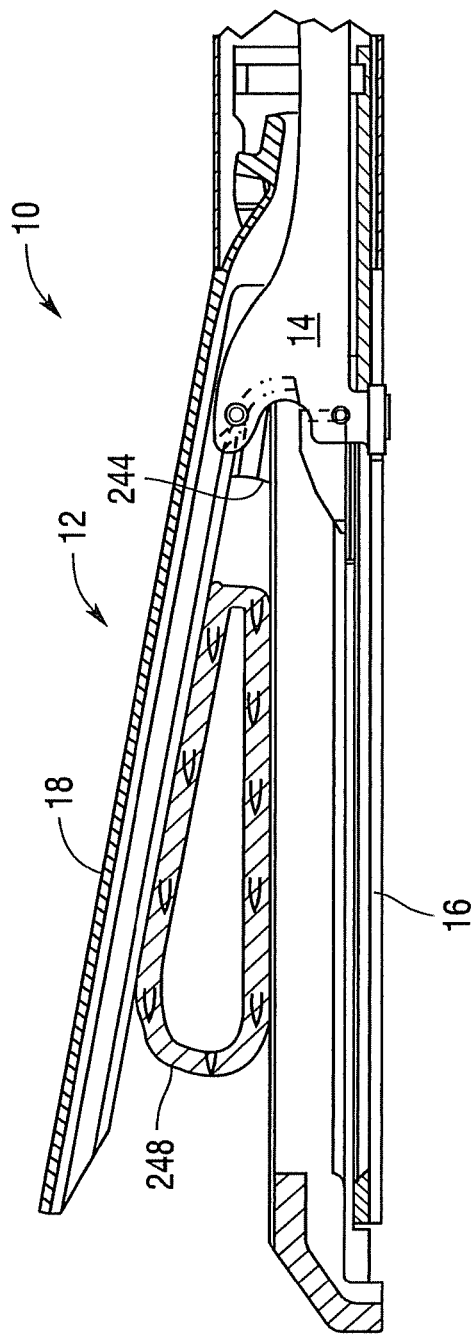
FIG. 35 is a side elevation section view of the surgical stapling and severing instrument of FIG. 1 taken along the longitudinal centerline of the end effector in a partially closed but unclamped position gripping tissue.

In use, the surgical stapling and severing instrument 10 is used as depicted in FIGS. 1-2 and 35-41. In FIGS. 1-2, the instrument 10 is in its start position, having had an unfired, fully loaded staple cartridge 300 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 300 and the anvil 18, as depicted in FIG. 35.

Figure 36:
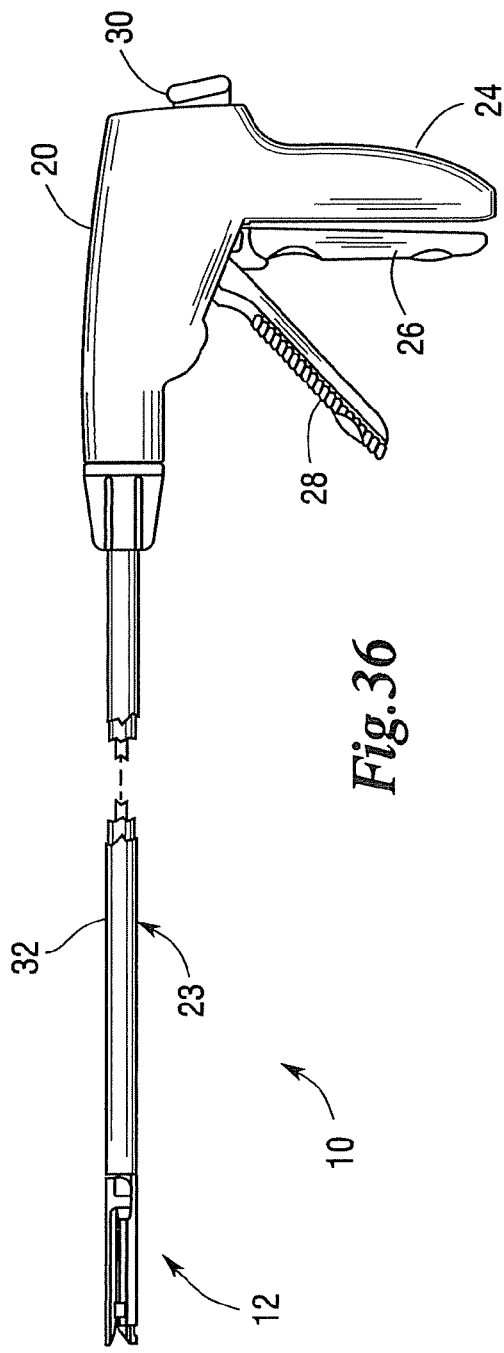
FIG. 36 depicts a partially cut away side elevational view of the surgical stapling and severing instrument of FIG. 1 in the closed or clamped position.
Figure 37:
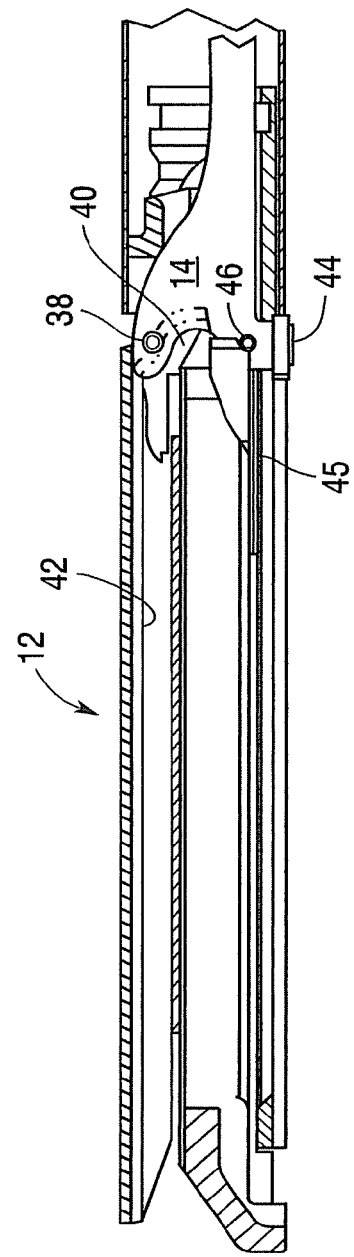
FIG. 37 depicts a side elevation view of the surgical stapling and severing instrument of FIG. 1 in the closed or clamped position with tissue properly compressed.

With reference to FIGS. 36 and 37, the clinician then moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the elongate channel 16 is affirmatively engaged about the channel slot 45 by the middle pin 46 and the firing bar cap 44.

With reference to FIGS. 38 and 39, after tissue clamping has occurred, the clinician moves the firing trigger 28 proximally causing the firing bar 14 to move distally into the end effector 12. In particular, the middle pin 46 enters the staple cartridge 300 through the firing drive slot 47 to effect the firing of the staples 222 (not shown in FIGS. 38 and 39) via wedge sled 400 toward the anvil 18. The lowermost pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the elongate channel 16 throughout its distal firing movement.

Figure 40:
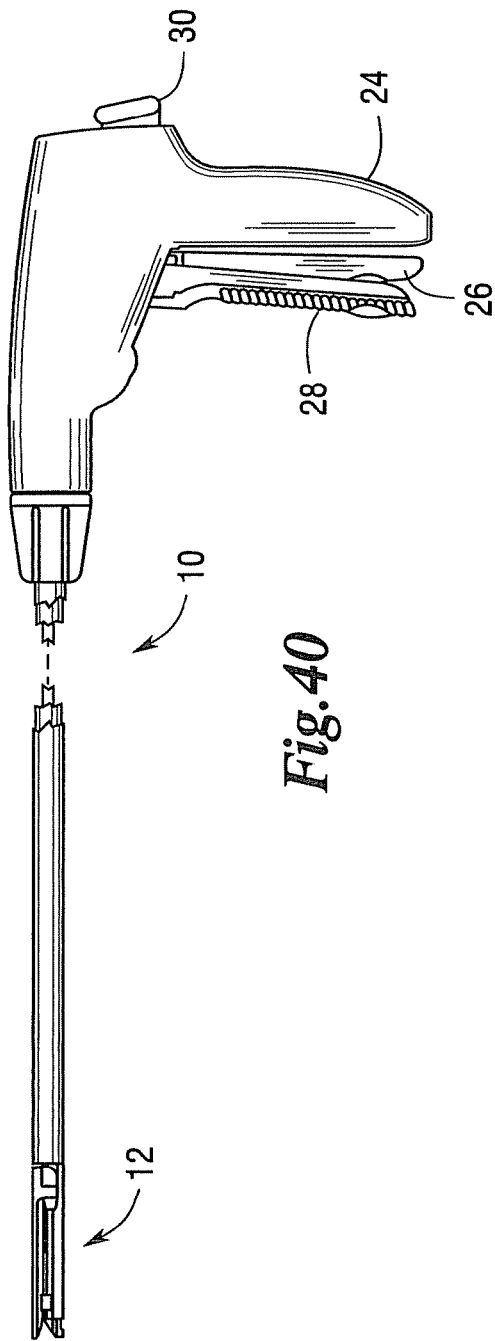
FIG. 40 depicts a view in centerline section of the distal end of the surgical stapling and severing instrument of FIG. 1 in a fully fired position.
Figure 41:
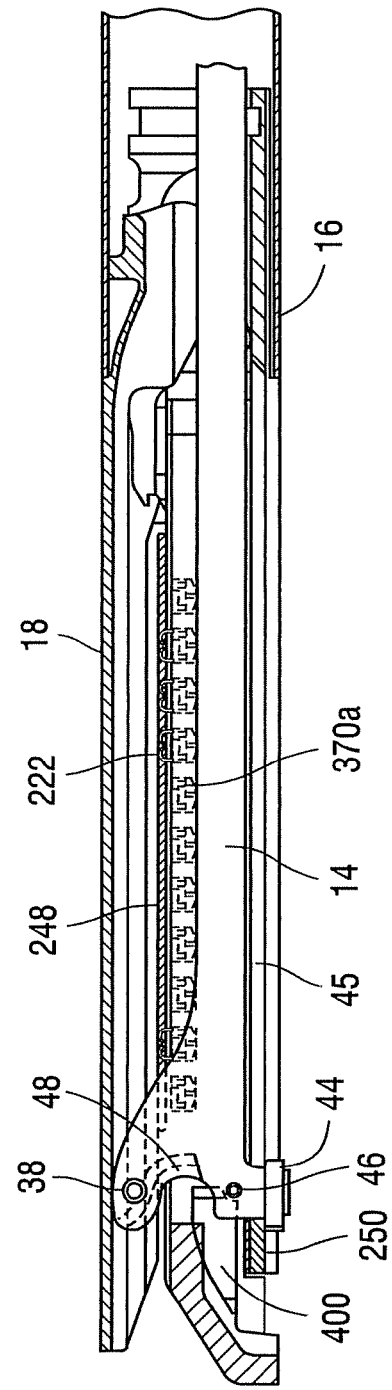
FIG. 41 is a partially cut-away side elevational view of the surgical stapling and severing instrument of FIG. 1 in a full fired position.

With reference to FIGS. 40 and 41, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is complete by releasing the firing trigger 28 and by then depressing the release button 30 while simultaneously squeezing the closure trigger 26 to open the end effector 12.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical staple cartridge for use with a surgical stapling instrument that includes an anvil that includes at least one tissue stop portion thereon, the surgical staple cartridge comprising:
   a cartridge body configured to be operably seated in a cartridge supporting portion of the surgical stapling instrument to confront a staple forming surface on the anvil when the anvil is moved to a closed position;
   a plurality of first staple drivers movably supported within the cartridge body, each first staple driver defining a first staple support cradle for supporting a first surgical staple thereon to define a linear row of first surgical staples within the cartridge body; and
   a plurality of second staple drivers movably supported within the cartridge body, each second staple driver defining a second staple support cradle for supporting a second surgical staple thereon to define another linear row of second surgical staples within the cartridge body and wherein a proximal-most first driver and a proximal-most second driver are configured and positioned within the cartridge body such that at least a portion of one first surgical staple and at least a portion of one second surgical staple are located proximal to a distal end of at least one of the tissue stop portions on the anvil when the first and second surgical staples are driven into forming contact with the staple forming surface on the anvil and such that the first surgical staples have a formed staple height that differs from a formed height of the second surgical staples.

2. The surgical staple cartridge of claim 1 wherein each first staple support cradle is located a first staple forming distance from a corresponding portion of the staple forming surface on the anvil and each second staple support cradle is located a second staple forming distance from another corresponding portion of the staple forming surface and wherein the first staple forming distance is different from the second staple forming distance.

3. The surgical staple cartridge of claim 1 wherein each said first staple driver supports at least two of said first surgical staples thereon.

4. The surgical staple cartridge of claim 1 further comprising an elongate slot in the cartridge body and wherein the plurality of first staple drivers are configured to support said linear row of first surgical staples within the cartridge body on each side of the elongate slot and wherein the plurality of second staple drivers are configured to support said another linear row of second surgical staples within the cartridge body on each side of said elongate slot.

5. The surgical staple cartridge of claim 4 wherein each said first driver is configured to support two first surgical staples thereon that are linearly offset from each other.

6. The surgical staple cartridge of claim 5 wherein the first staple drivers on one side of the elongate slot are located between the elongate slot and the second staple drivers located on a same side of the elongate slot.

7. The surgical staple cartridge of claim 5 wherein each of the second staples supported on one side of the elongate slot is laterally aligned with a corresponding first staple located on a same side of the elongate slot.

8. The surgical staple cartridge of claim 1 wherein a number of first staple drivers exceed a number of second staple drivers.

9. The surgical staple cartridge of claim 1 further comprising a wedge sled supported within said cartridge body for driving contact with each of the first and second staple drivers upon application of a firing motion thereto.

10. The surgical staple cartridge of claim 1 wherein all of the first and second surgical staples have substantially the same unformed size and shape.

11. A surgical staple cartridge for use with a surgical stapling instrument that includes an anvil that includes at least one tissue stop portion thereon, the surgical staple cartridge comprising:
    a cartridge body configured to be operably seated in a cartridge supporting portion of the surgical stapling instrument to confront a staple forming surface on the anvil when the anvil is moved to a closed position, the cartridge body including an elongate slot for receiving a cutting portion of the surgical stapling instrument;
    a plurality of first staple drivers operably supported in said cartridge body and configured to eject surgical staples into forming contact with the staple forming surface on the anvil in at least two linear rows located on at least one lateral side of the elongate slot such that at least a portion of a proximal-most surgical staple in each said linear row is located proximal to a distal end of at least one of the tissue stop portions on the anvil when the surgical staples are ejected into forming contact with the staple forming surface on the anvil; and
    a plurality of second staple drivers movably supported in said cartridge body and configured to eject other surgical staples in another linear row located on said at least one lateral side of the elongate slot into forming contact with the staple forming surface on the anvil such that a proximal-most other surgical staple in said another linear row is distal to the distal end of the at least one tissue stop portion and wherein the other surgical staples ejected by the second staple drivers have a formed staple height that differs from a formed staple height of the surgical staples in at least one said linear row of surgical staples ejected by said first staple drivers.

12. The surgical staple cartridge of claim 11 wherein each said first staple driver operably supports two said surgical staples.

13. The surgical staple cartridge of claim 11 wherein the formed heights of the surgical staples in one said linear row of said at least two linear rows differs from other formed heights of the surgical staples in the other said linear row of said at least two linear rows of staples on a same lateral side of the elongate slot.

14. The surgical staple cartridge of claim 13 wherein a formed height of each of the surgical staples in each said linear row differs from the formed heights of the staples in the other said linear rows on a same side of the elongate slot.

15. The surgical staple cartridge of claim 11 wherein the at least two linear rows of surgical staples configured to be ejected by said plurality of first staple drivers on one side of said elongate slot are closer to the elongate slot than the other said linear row of other surgical staples configured to be ejected by said plurality of second staple drivers on a same side of the elongate slot.

16. The surgical staple cartridge of claim 11 wherein all of the surgical staples and other surgical staples have substantially the same unformed size and shape.

17. The surgical staple cartridge of claim 11 wherein a number of first staple drivers on one side of the elongate slot exceed a number of second staple drivers on a same side of the elongate slot.

18. The surgical staple cartridge of claim 11 further comprising a wedge sled supported within said cartridge body for driving contact with each of the first and second staple drivers upon application of a firing motion thereto.

19. A surgical stapling device, comprising:
a firing system for generating firing motions;
a closure system for generating opening and closing motions;
an implement portion operably interfacing with the firing and closure systems, the implement portion comprising:
an elongate channel operably interfacing with the firing and closure systems and configured to support a staple cartridge therein;
an anvil pivotally coupled to the elongate channel and being movable between open and closed positions relative to the elongate channel in response to closure and opening motions from the closure system;
a firing device including a distally presented cutting edge longitudinally movable within the elongate channel in response to firing motions applied thereto by the firing system; and
a staple cartridge comprising:
a cartridge body supportable within the elongate channel, said cartridge body having a non-planar deck surface configured to confront a staple forming portion of the anvil when the anvil is in a closed position;
a plurality of first staple drivers movably supported within said cartridge body and being sequentially movable from an unactuated position to an actuated position upon sequential interaction with the firing device, each said first staple driver defining a first staple support cradle therein for supporting a staple thereon, each said first staple support cradle located a first staple forming distance from a corresponding portion of the staple forming portion of the closed anvil; and
a plurality of second staple drivers movably supported within said cartridge body and being laterally spaced from said first staple drivers, each said second staple driver being sequentially movable from another unactuated position to another actuated position upon sequential interaction with the firing device, each said second staple driver defining a second staple support cradle therein for supporting another staple thereon, each said second staple support cradle located a second staple forming distance from another corresponding portion of the staple forming portion of the closed anvil that corresponds to the second staple support cradle and wherein said second staple forming distance differs in magnitude from said first staple forming distance.

20. The surgical stapling device of claim 19 wherein each said first staple driver supports at least two of said staples thereon.

21. A surgical stapling system, comprising:
a firing system configured to generate a firing motion; and
an implement portion configurable in an open configuration and a clamped configuration, said implement portion comprising:
a distal end;
an anvil comprising a staple forming portion;
a firing member including a distally presented cutting edge movable toward said distal end in response to said firing motion generated by said firing system; and
a staple cartridge, comprising:
a cartridge body comprising a non-planar deck surface configured to confront said staple forming portion of said anvil; and
a plurality of staple drivers movably supported within said cartridge body, wherein said staple drivers are sequentially movable from an unactuated position to an actuated position by said firing member, wherein said staple drivers comprise:
a first longitudinal row of first staple support cradles, wherein each said first staple support cradle is configured to support a first staple thereon, wherein said first staple support cradles are located a first staple forming distance from a first corresponding portion of said staple forming portion that corresponds to said first staple support cradles when said implement portion is in said clamped configuration; and
a second longitudinal row of second staple support cradles, wherein each said second staple support cradle is configured to support a second staple thereon, wherein said second staple support cradles are located a second staple forming distance from a second corresponding portion of said staple forming portion that corresponds to said second staple support cradles when said implement portion is in said clamped configuration, and wherein said second staple forming distance differs in magnitude from said first staple forming distance.

* * * * *